United States Patent [19]
Rogers et al.

[11] Patent Number: 6,115,488
[45] Date of Patent: Sep. 5, 2000

[54] METHOD AND SYSTEM FOR COMBINING AUTOMATED DETECTIONS FROM DIGITAL MAMMOGRAMS WITH OBSERVED DETECTIONS OF A HUMAN INTERPRETER

[75] Inventors: Steven K. Rogers, Beavercreek; Philip Amburn, Dayton; Telford S. Berkey, London; Randy P. Broussard, Huber Heights; Martin P. Desimio, Fairborn; Jeffrey W. Hoffmeister, Beavercreek, all of Ohio; Edward M. Ochoa, San Antonio, Tex.; Thomas P. Rathbun, Beavercreek, Ohio; John E. Rosenstengel, Huber Heights, Ohio

[73] Assignee: Qualia Computing, Inc., Beavercreek, Ohio

[21] Appl. No.: 09/418,382

[22] Filed: Oct. 14, 1999

Related U.S. Application Data

[62] Division of application No. 09/141,802, Aug. 28, 1998, Pat. No. 5,999,639.

[60] Provisional application No. 60/057,801, Aug. 28, 1997, provisional application No. 60/066,996, Nov. 28, 1997, and provisional application No. 60/076,760, Mar. 3, 1998.

[51] Int. Cl.$^7$ .................................................. G06K 9/00
[52] U.S. Cl. ............................................ 382/132; 128/922
[58] Field of Search .................................... 382/128, 132, 382/309, 311; 128/920, 922; 378/37; 706/924

[56] References Cited

U.S. PATENT DOCUMENTS

| | | | |
|---|---|---|---|
| 4,453,266 | 6/1984 | Bacus | 382/6 |
| 4,723,553 | 2/1988 | Miwa et al. | 128/660 |
| 4,736,439 | 4/1988 | May | 382/54 |
| 4,747,156 | 5/1988 | Wahl | 382/54 |
| 4,907,156 | 3/1990 | Doi et al. | 364/413.13 |
| 5,133,020 | 7/1992 | Giger et al. | 382/6 |

(List continued on next page.)

OTHER PUBLICATIONS

Winsberg, M.D., F., et al., "Detection of Radiographic Abnormalities in Mammograms by Means of Optical Scanning and Computer Analysis," *Radiology*, vol. 89, Aug. 1967, (pp. 211–215).

Ackerman, L.V., "Computer Classification of Radiographs and Xerograms of the Breast," Ph.D. Dissertation, University of Illinois at the Medical Center, Oct. 1970.

Hall, E.L., et al., "A Survey of Preprocessing and Feature Extraction Techniques for Radiographic Images," *IEEE Transactions on Computers*, vol. C–20, No. 9, Sep. 1971, (pp. 1032–1044).

Ackerman, L.V., et al., "Breast Lesion Classification by Computer and Xeroradiograph," *Cancer*, vol. 30, No. 4, Oct. 1972, (pp. 1025–1035).

(List continued on next page.)

*Primary Examiner*—Andrew W. Johns
*Attorney, Agent, or Firm*—Biebel & French

[57] ABSTRACT

A method and system for detecting and displaying clustered microcalcifications in a digital mammogram, wherein a single digital mammogram is first automatically cropped to a breast area sub-image which is then processed by means of an optimized Difference of Gaussians filter to enhance the appearance of potential microcalcifications in the sub-image. The potential microcalcifications are thresholded, clusters are detected, features are computed for the detected clusters, and the clusters are classified as either suspicious or not suspicious by means of a neural network. Thresholding is preferably by sloping local thresholding, but may also be performed by global and dual-local thresholding. The locations in the original digital mammogram of the suspicious detected clustered microcalcifications are indicated. Parameters for use in the detection and thresholding portions of the system are computer-optimized by means of a genetic algorithm. The results of the system are optimally combined with a radiologist's observation of the original mammogram by combining the observations with the results, after the radiologist has first accepted or rejected individual detections reported by the system.

7 Claims, 28 Drawing Sheets

U.S. PATENT DOCUMENTS

| | | | |
|---|---|---|---|
| 5,212,637 | 5/1993 | Saxena | 364/413.26 |
| 5,260,871 | 11/1993 | Goldberg | 364/413.02 |
| 5,268,967 | 12/1993 | Jang et al. | 382/6 |
| 5,289,374 | 2/1994 | Doi et al. | 364/413.13 |
| 5,291,560 | 3/1994 | Daugman | 382/2 |
| 5,331,550 | 7/1994 | Stafford et al. | 364/413.02 |
| 5,343,390 | 8/1994 | Doi et al. | 364/413.16 |
| 5,359,513 | 10/1994 | Kano et al. | 364/413.23 |
| 5,365,429 | 11/1994 | Carman | 364/413.13 |
| 5,388,143 | 2/1995 | MacMahon | 378/206 |
| 5,452,367 | 9/1995 | Bick et al. | 382/128 |
| 5,463,548 | 10/1995 | Asada et al. | 364/413.02 |
| 5,491,627 | 2/1996 | Zhang et al. | 364/413.2 |
| 5,537,485 | 7/1996 | Nishikawa et al. | 382/130 |
| 5,572,565 | 11/1996 | Abdel-Mottaleb | 378/37 |
| 5,574,799 | 11/1996 | Bankman et al. | 382/132 |
| 5,579,360 | 11/1996 | Abdel-Mottaleb | 378/37 |
| 5,586,160 | 12/1996 | Mascio | 378/37 |
| 5,598,481 | 1/1997 | Nishikawa et al. | 382/130 |
| 5,615,243 | 3/1997 | Chang et al. | 378/37 |
| 5,622,171 | 4/1997 | Asada et al. | 128/653.1 |
| 5,625,717 | 4/1997 | Hashimoto et al. | 382/260 |
| 5,627,907 | 5/1997 | Gur et al. | 382/132 |
| 5,633,948 | 5/1997 | Kegelmeyer, Jr. | 382/132 |
| 5,638,458 | 6/1997 | Giger et al. | 382/132 |
| 5,657,362 | 8/1997 | Giger et al. | 378/37 |
| 5,661,820 | 8/1997 | Kegelmeyer, Jr. | 382/226 |
| 5,666,434 | 9/1997 | Nishikawa et al. | 382/128 |
| 5,668,888 | 9/1997 | Doi et al. | 382/132 |
| 5,673,332 | 9/1997 | Nishikawa et al. | 382/128 |
| 5,729,620 | 3/1998 | Wang | 382/128 |
| 5,729,662 | 3/1998 | Rozmus | 395/23 |
| 5,732,697 | 3/1998 | Zhang et al. | 128/630 |
| 5,740,266 | 4/1998 | Weiss et al. | 382/128 |
| 5,740,267 | 4/1998 | Echerer et al. | 382/132 |
| 5,740,268 | 4/1998 | Nishikawa et al. | 382/132 |
| 5,757,953 | 5/1998 | Jang | 382/132 |
| 5,761,334 | 6/1998 | Nakajima et al. | 382/132 |
| 5,768,333 | 6/1998 | Abdel-Mottaleb | 378/37 |
| 5,768,406 | 6/1998 | Abdel-Mottaleb | 382/132 |
| 5,769,074 | 6/1998 | Barnhill et al. | 128/630 |
| 5,779,634 | 7/1998 | Ema et al. | 600/407 |
| 5,799,100 | 8/1998 | Clarke et al. | 382/132 |
| 5,815,591 | 9/1998 | Roehrig et al. | 382/130 |
| 5,825,910 | 10/1998 | Vafai | 382/132 |
| 5,825,936 | 10/1998 | Clarke et al. | 382/261 |
| 5,828,774 | 10/1998 | Wang | 382/128 |
| 5,832,103 | 11/1998 | Giger et al. | 382/130 |
| 5,857,030 | 1/1999 | Gaborski et al. | 382/132 |
| 5,917,929 | 6/1999 | Marshall et al. | 382/128 |
| 5,999,639 | 12/1999 | Rogers et al. | 382/132 |

OTHER PUBLICATIONS

Haralick, R., et al., "Textural Features for Image Classification," *IEEE Transactions on Systems, Man, and Cybernetics*, vol. SMC–3, No. 6, Nov. 1973, (pp. 610–621).

Ballard, D., et al., "Tumor Detection in Radiographs," *Computers and Biomedical Research*, vol. 6, 1973, (pp. 299–321).

Ackerman, L.V., et al., "Classification of Benign and Malignant Breast Tumors on the Basis of 36 Radiographic Properties," *Cancer*, vol. 31, No. 2, 1973, (p. 138).

Chang, N–C., "Computer Characterization of Calcifications for Breast Cancer Detection—A Feasibility Study," Master's Thesis, Department of Electrical Engineering, University of Cincinnati, 1973.

Wes, Ph.D., W.G. "Evaluation of Mammographic Calcifications Using a Computer Program," Work in Progress, *Radiology*, vol. 116, Sep. 1975, (pp. 717–720).

Kimme, C., et al., "Automatic Detection of Suspicious Abnormalities in Breast Radiographs," *Data Structures, Computer Graphics and Pattern Recognition*, 1975, (pp. 427–447).

Ting, Y.C., "A Computer Pattern Recognition System for Breast Cancer Detection," Master's Thesis, University of Cincinnati, 1975.

Millis, R.R., et al., "The Detection and Significance of Calcifications in the Breast: A Radiological and Pathological Study," *British Journal of Radiology*, vol. 49, No. 577, Jan. 1976, (pp. 12–26).

Spiesberger, W., et al., "Outlining of Microcalcifications by Computer–Assisted Mammogram Inspection," *Medicamundi*, vol. 22, No. 3, 1977, (pp. 32–34).

Spiesberger, W., "Mammogram Inspection by Computer," *IEEE Transactions on Biomedical Engineering*, vol. BME–26, No. 4, Apr. 1979, (pp. 213–219).

Kimme–Smith, C., et al., "Toward Reliable Measurements of Breast Parenchymal Patterns," *Proceedings of Sixth Conference on Computer Application in Radiology and Computer –Aided Analysis of Radiology Images*, Jun. 1979, (pp. 118–121).

Hand, W., et al., "Computer Screening of Xeromammograms: A Technique for Defining Suspicious Areas of the Breast," *Computers and Biomedical Research*, vol. 12, 1979, (pp. 445–460).

Fox, S.H., et al., "Computer Analysis of Mammographic Microcalcifications: Global Approach," *Proceedings of the IEEE 5th International Conference on Pattern Recognition*, 1980, (pp. 624–631).

Semmlow, J.L., et al., "A Fully Automated System for Screening Xeromammograms," *Computers and Biomedical Research*, vol. 13, 1980, (pp. 350–362).

Dhawan, A.P., et al., "Enhancement of Mammographic Features by Optimal Adaptive Neighborhood Image Processing," *IEEE Transactions on Medical Imaging*, vol. MI–5, No. 1, Mar. 1986, (pp. 8–15.).

Dhawan, A.P., et al., Correction to "Enhancement of Mammographic Features by Optimal Adaptive Neighborhood Image Processing," *IEEE Transactions on Medical Imaging*, vol. MI–5, No. 2, Jun. 1986, (p. 120).

Bhanu, B., "Automatic Target Recognition: State of the Art Survey," *IEEE Transactions on Aerospace and Electronic Systems*, vol. AES–22, No. 4, Jul. 1986, (pp. 364–379).

Metz, Ph.D., C.E., "ROC Methodology in Radiologic Imaging," *Investigative Radiology*, vol. 21, No. 9, Sep. 1986 (pp. 720–733).

Lippmann, R.P., "An Introduction to Computing with Neural Nets," *IEEE ASSP Magazine*, vol. 96, Apr. 1987 (pp. 4–22).

Chan, H–P, et al., "Image Feature Analysis and Computer–Aided Diagnosis in Digital Radiography. I. Automated Detection of Microcalcifications in Mammography," *Med. Phys.*, vol. 14, No. 4, Jul./Aug. 1987, (pp. 538–548).

Kahn, E., et al., "Computer Analysis of Breast Calcifications in Mammographic Images," *Proceedings of the International Symposium on Computer Assisted Radiology '87*, Lemke, U., et al., editors, 1987, (pp. 729–733).

Chan, H–P, et al., "Original Investigations: Computer–Aided Detection of Microcalcifications in Mammograms—Methodology and Preliminary Clinical Study," *Investigative Radiology*, vol. 23, No. 7, Jul. 1988, (pp. 664–671).

Fam, B.W., et al., "Algorithm for the Detection of Fine Clustered Calcifications on Film Mammograms," *Radiology*, vol. 169, No. 1, Oct. 1988, (pp. 333–337).

Fam, B.W., et al., "The Detection of Calcification Clusters in Film–Screen Mammograms; A Detailed Algorithmic Approach" *Medical Imaging II*, vol. 914, 1988, (pp. 620–634).

Dhawan, A.P., et al., "Mammographic Feature Enhancement by Computerized Image Processing," *Computer Methods and Programs in Biomedicine*, vol. 27, 1988 (pp. 23–35).

Davies, D.H., et al., "Automatic Detection of Microcalcifications in Digital Mammograms Using Local Area Thresholding Techniques," *SPIE's Conference on Medical Imaging III Image Processing*, vol. 1092, Newport Beach, CA, Jan. 31–Feb. 3, 1989, (pp. 153–159).

Lai, S.M., et al., "On Techniques for Detecting Circumscribed Masses in Mammograms," *IEEE Transactions on Medical Imaging*, vol. 8, No. 4, Dec. 1989, (pp. 377–386.

Davies, D.H., et al., "Automatic Detection of Clusters of Calcifications in Digital Mammograms," *Proceedings of the International Symposium on Computer Assisted Radiology*, Lemke, H.U., et al., editors, 1989, (pp. 180–184).

Ayer, K.W. et al., "Foward Looking Infrared Image Segmentation and Pattern Recognition Using Gabor Transform and Joint Transform Correlation Techniques," Wright Laboratories, Air Force Institute of Technology, Technical Report, Mar. 1990.

Davies, D.H., et al., "Automatic Computer Detection of Clustered Calcification in Digital Mammograms," *Phys. Med. Biol.*, vol. 35, No. 8, Apr. 1990, (pp. 1111–1118).

Boone, J.M., et al., "Neural Network in Radiologic Diagnosis," *Investigative Radiology*, vol. 25, No. 9 Sep. 1990, (pp. 1012–1016).

Brzakovic, D., et al., "An Approach to Automated Detection of Tumors in Mammograms" *IEEE Transactions on Medical Imaging*, vol. 9, No. 3, Sep. 1990, (pp. 233–241).

Rogers, S.K., et al., *An Introduction to Biological and Artificial Neural Networks*, Oct. 23, 1990, (pp. 47–61).

Chan, Ph.D., H–P, et al., "Improvement in Radiologists' Detection of Clustered Microcalcifications on Mammograms—The Potential of Computer–Aided Diagnosis," *Investigative Radiology*, vol. 25, No. 10, Oct. 1990, (pp. 1102–1110).

Veronin, C.P., et al., "An Optical Image Segmentor Using Wavelet Filtering Techniques as the Front End of a Neural Network Classifier," *SPIE's International Conference on Applications of Artificial Neural Networks*, vol. 1469, Apr. 1991, (pp. 281–291).

Lau, T.K., et al., "Automated Detection of Breast Tumors Using the Asymmetry Approach," *Computers and Biomedical Research*, vol. 24, No. 3, Jun. 1991, (pp. 273–295).

Yin, F.F., et al., "Computerized Detection of Masses in Digital Mammograms: Analysis of Bilateral Subtraction Images," *Med. Phys.*, vol. 18, No. 5, Sep./Oct. 1991, (pp. 955–963).

Zhang, W., et al., "Image Processing of Human Corneal Endothelium Based on a Learning Network," *Applied Optics*, vol. 30, No. 29, Oct. 10, 1991, (pp. 4211–4217).

Laing, J., et al., "Gabor and Multiresolution Wavelet Decomposition Analysis of the Kanisza Triangle Illusion," for Wright Lab Target Recognition Group, Nov. 1991.

Kimme–Smith, Ph.D., C., "New and Future Developments in Screen–Film Mammography Equipment and Techniques," *Radiologic Clinics of North America*, vol. 30, No. 1, Jan. 1992, (pp. 55–66).

Veronin, C.P., et al., "Optical Image Segmentation Using Neural–Based Wavelet Filtering Techniques," *Optical Engineering*, vol. 31, No. 2, Feb. 1992, (pp. 287–294).

Wu, Y., et al., "Computerized Detection of Clustered Microcalcifications in Digital Mammograms: Applications of Artificial Neural Networks," *Medical Physics*, vol. 19, No. 3, May/Jun. 1992, (pp. 555–560).

Ng, S.L., et al., "Automated Detection and Classification of Breast Tumors," *Computers and Biomedical Research*, vol. 25, 1992 (pp. 218–237).

Dhawan, A.P., et al., "Artificial Neural Network Based Classification of Mammographic Microcalcifications Using Image Structure Features," *Proceedings of SPIE's Conference on Biomedical Image Processing and Biomedical Visualization*, San Jose, vol. 1905, Feb. 1–4, 1993, (pp. 820–831).

Wu, Y., et al., "Artificial Neural Networks in Mammography: Application to Decision Making in the Diagnosis of Breast Cancer," *Radiology*, vol. 187, No. 1, Apr. 1993, (pp. 81–87).

Woods, K.S., et al, "Comparative Evaluation of Pattern Recognition Techniques for Detection of Microcalcifications in Mammography," *Computerized Medical Imaging and Graphics*, vol. 16, No. 5, May 1993, (pp. 1417–1436).

Fletcher, S.W., et al., "Report of the International Workshop on Screening for Breast Cancer," *Journal of the National Cancer Institute*, vol. 85, No. 20, Oct. 20, 1993, (pp. 1644–1656).

Anand, R., et al., "An Improved Algorithm for Neural Network Classification of Imbalanced Training Sets," *IEEE Transactions on Neural Networks*, vol. 4, No. 6, Nov. 1993, (pp. 962–969).

Dengler, J., et al., "Segmentation of Microcalcifications in Mammograms," *IEEE Transactions on Medical Imaging*, vol. 12, No. 4, Dec. 1993, (pp. 634–642).

Giger, Ph.D., M.L., "Computer–Aided Diagnosis," *RSNA Categorical Course in Physics 1993*, 1993, (pp. 283–298).

Nishikawa, R.M., et al., "Effect of Case Selection on the Performance of Computer–Aided Detection Schemes," *Med. Phys.*, vol. 21, No. 2, Feb. 1994, (pp. 265–269).

Yin, F.F., et al., "Computerized Detection of Masses in Digital Mammograms: Investigation of Feature–Analysis Techniques," *Journal of Digital Imaging*, vol. 7, No. 1, Feb. 1994, (pp. 18–26).

Kegelmeyer, Jr. Ph.D., W.P., et al., "Computer–Aided Mammographic Screening for Spiculated Lesions," *Radiology*, vol. 191, No. 2, May 1994, (pp. 331–337).

Bårman, H., et al. "Feature Extraction For Computer–Aided Analysis of Mammograms," *State of the Art Digital Mammographic Image Analysis*, Boyer, K.W., et al., editors, 1994, (pp. 128–147).

Chitre, Y., et al., "Artificial Neural Network Based Classification of Mammographic Microcalcifications Using Image Structure Features," *State of the Art in Digital Mammographic Image Analysis*, Boyer, K.W., et al., editors, 1994, (pp.167–197).

Giger, M.L., et al., "Computerized Characterization of Mammographic Masses: Analysis of Spiculation," *Cancer Letters*, vol. 77, 1994, (pp. 201–211).

Kegelmeyer, Jr., W.P., "Evaluation of Stellate Lesion Detection in a Standard Mammogram Data Set," *State of the Art in Digital Mammographic Image Analysis*, Boyer, K.W. et al., editors, 1994, (pp. 262–279).

Lidbrink, E.K., et al., "The General Mammography Screening Program in Stockholm: Organisation and First–Round Results," *Acta Oncologica*, vol. 33, No. 4, 1994, (pp. 353–358).

Nishikawa, R.M., "Computer–Aided Detection and Diagnosis of Masses and Clustered Microcalcifications from Digital Mammograms," *State of the Art in Digital Mammographic Image Analysis*, Boyer, K.W., et al., editors, 1994, (pp. 82–102).

Petrosian, A., et al., "Computer–Aided Diagnosis in Mammography: Classification of Mass and Normal Tissue by Texture Analysis," *Phys. Med. Biol.*, vol. 39, 1994, (pp. 2273–2288).

Shen, L., et al., "Detection and Classification of Mammographic Calcifications," *State of the Art in Digital Mammographic Image Analysis*, Boyer, K.W., et al., editors, 1994, (pp. 198–212).

Wilding, P., et al., "Application of Backpropagation Neural Networks to Diagnosis of Breast and Ovarian Cancer," *Cancer Letters*, vol. 77, 1994, (pp. 145–153).

Woods, K.S., et al., "Comparative Evaluation of Pattern Recognition Techniques for Detection of Microcalcifications in Mammography," *State of the Art in Digital Mammographic Image Analysis*, Boyer, K.W., et al., editors 1994, (pp. 213–231).

Chan, H–P, et al., "Computer–Aided Classification of Mammographic Masses and Normal Tissue: Linear Discriminant Analysis in Texture Feature Space," *Phys. Med. Biol.*, vol. 40, Feb. 1995, (pp. 857–876).

Hojjatoleslami, S.A., et al., "Automatic Detection of Calcification in Mammograms," 5th International Conference on Image Processing and Its Applications, vol. 410, Jul. 1995. (pp. 139–143).

Li, H.D., et al, "Markov Random Field for Tumor Detection in Digital Mammography," *IEEE Transactions on Medical Imaging*, vol. 14, No. 3, Sep. 1995, (pp. 565–576).

Huo Z., et al., "Analysis of Spiculation in the Computerized Classification of Mammographic Masses," *Med. Phys.*, vol. 22, No. 10, Oct. 1995, (pp. 1569–1579).

Bick, U., et al., "Automated Segmentation of Digitized Mammograms," *Academic Radiology*, vol. 2, 1995, (pp. 1–9).

Feig, M.D., S.A, et al., "Digital Mammography, Computer–Aided Diagnosis, and Telemammography," *Radiologic Clinics of North America*, vol. 33, No. 6, Nov. 1995, (pp. 1205–1230).

Zheng, B., et al., "Computerized Detection of Masses from Digitized Mammograms: Comparison of Single–Image Segmentation and Bilateral–Image Subtraction," *Academic Radiology*, vol. 2, No. 12, Dec. 1995, (pp. 1056–1061).

Tahoces, P.G., et al., "Computer–Assisted Diagnosis: The Classification of Mammographic Breast Parenchymal Patterns," *Phys. Med. Biol.*, vol. 40, 1995, (pp. 103–117).

McCandless, D.A., et al., "Wavelet Detection of Clustered Microcalcifications," *SPIE*, vol. 2762 (date unknown), (pp. 388 et seq.).

Braccialarghe, D., et al., "Contrast Enhancement of Mammographic Features: A Comparison of Four Methods," *Optical Engineering*, vol. 35, No. 1, Jan. 1996, (pp. 76–80).

Sahiner, B., et al., "Classification of Mass and Normal Breast Tissue: Feature Selection Using a Genetic Algorithm," *Colloqium on Digital Mammography*, Feb. 1996, (pp. 379–384).

Chang, Y–H, et al., "Computerized Identification of Suspicious Regions for Masses in Digitized Mammograms," *Investigative Radiology*, vol. 31, No. 3, Mar. 1996, (pp. 146–153).

Giger, Ph.D., M., et al., "Image Processing and Computer–Aided Diagnosis," *Radiologic Clinics of North America*, vol. 34, No. 3, May 1996, (pp. 565–596).

Kocur, C.M., et al., "Using Neural Networks to Select Wavelet Features for Breast Cancer Diagnosis," *IEEE Engineering in Medicine and Biology*, May/Jun. 1996, (pp. 95–102).

Dhawan, A.P., et al., "Analysis of Mammographic Microcalcifications Using Gray–Level Image Structure Features," *IEEE Transactions on Medical Imaging*, vol. 15, No. 3, Jun. 1996, (pp. 246–259).

Pohlman, S., et al., "Quantitiative Classification of Breast Tumors in Digitized Mammograms," *Med. Phys.*, vol. 23, No. 8, Aug. 1996, (pp. 1337–1345).

Chang, Y–H., "Robustness of Computerized Identification of Masses in Digitized Mammograms," *Investigative Radiology*, vol. 31, No. 9, Sep. 1996, (pp. 563–568).

Cooley, T.R., "An Automated System for the Classification of Mammograms," Ph.D. Dissertation, Rutgers, the State University of New Jersey, Oct. 1996.

Petrick, N., et al., "Automated Detection of Breast Masses on Mammograms Using Adaptive Contrast Enhancement and Texture Classification," *Med. Phys.*, vol. 23, No. 10, Oct. 1996, (pp. 1685–1696).

Sahiner, B., et al., "Image Feature Selection by a Genetic Algorithm: Application to Classification of Mass and Normal Breast Tissue," *Med. Phys.*, vol. 23, No. 10, Oct. 1996, (pp. 1671–1684).

Bick, U., et al., "Density Correction of Peripheral Breast Tissue on Digital Mammograms," *RadioGraphics*, vol. 16, No. 6, Nov. 1996, (pp. 1403–1411).

Ochoa, E.M., "Clustered Microcalcification Detection Using Optimized Difference of Gaussians," Master's Thesis, Department of the Air Force, Air University, Air Force Institute of Technology, Dec. 1996.

Zheng, B., et al., "On the Reporting of Mass Contrast in CAD Research," *Med. Phys.*, vol. 23, No. 12, Dec. 1996, (pp. 2007–2009).

Chen, L., et al., "Morphological Filtering and Multiresolution Fusion for Mammographic Microcalcifications Detection," Proceedings of SPIE's Conference on Image Processing, Newport Beach, vol. 3034, Feb. 25–28, 1997, (pp. 938–947).

Freedman, M., et al., "Classification of False Positive Findings on Computer Aided Detection of Breast Microcalcifications," Proceedings of SPIE's Conference on Image Processing, Newport Beach, vol. 3034, Feb. 25–28, 1997 (pp. 853–859).

Gavrielides, M.A., et al., "Automatic Shape Analysis and Classification of Mammographic Calcifications," Proceedings of SPIE's Conference on Image Processing, Newport Beach, vol. 3034, Feb. 25–28, 1997, (pp. 869–876).

Li, H., et al., "Mammographic Mass Detection by Stochastic Modeling and a Multi–Modular Neural Network," Proceedings of SPIE's Conference on Image Porcessing, Newport Beach, vol. 3034, Feb. 25–28, 1997, (pp. 480–490).

Sahiner, B., et al., "Characterization of Masses on Mammograms: Significance of the Use of the Rubber–Band Straightening Transform," Proceedings of SPIE's Conference on Image Processing, Newport Beach, vol. 3034, Feb. 25–28, 1997 (pp. 491–499).

Wu, C.Y., et al., "Image Feature Analysis for Classification of Microcalcifications in Digital Mammography: Neural Networks and Genetic Algorithms," Proceedings of SPIE's Conference on Image Processing, Newport Beach, vol. 3034, Feb. 25–28, 1997 (pp. 501–509).

Zheng, Y., et al., "Reducing Breast Biopsies by Ultrasonographic Analysis and a Modified Self–Organizing Map," Proceedings of SPIE's Conference on Image Processing, Newport Beach, vol. 3033, Feb. 25–28, 1997 (pp. 384–391).

Rogers, S.K., "Introduction to Artificial Neural Networks," *Fundamentals of Artificial Neural Networks*, Apr. 1997, (pp. 1–41).

Zheng, Y., et al., "Reduction of Breast Biopsies with a Modified Self–Organizing Map," *IEEE Transactions on Neural Networks*, vol. 8, No. 6, Nov. 1997, (pp. 1386–1396).

Anastasio, M.A., et al., "Optimization and FROC Analysis of Rule–Based Detection Schemes Using a Multiobjective Approach," Correspondence in *IEEE Transactions on Medical Imaging*, Aug. 26, 1998.

Fig. 12

|          | p(x,y-1) |          |
|----------|----------|----------|
| p(x-1,y) | p(x,y)   | p(x+1,y) |
|          | p(x,y+1) |          |

METHOD AND SYSTEM FOR COMBINING AUTOMATED DETECTIONS FROM DIGITAL MAMMOGRAMS WITH OBSERVED DETECTIONS OF A HUMAN INTERPRETER

CROSS-REFERENCE TO RELATED APPLICATIONS

This application is a division of application Ser. No. 09/141,802, filed Aug. 28, 1998, now U.S. Pat. No. 5,999, 639, which claims the benefit of U.S. Provisional application Ser. No. 60/057,801, filed August 28, 1997, U.S. Provisional application Ser. No. 60/066,996, filed Nov. 28, 1997, and U.S. Provisional application Ser. No. 60/076,760, filed Mar. 3, 1998, the entire disclosures of all of which are incorporated herein by reference.

BACKGROUND OF THE INVENTION

1. Field of the Invention

This invention relates to a method and system for automated detection of clustered microcalcifications from digital images without reduction of radiologist sensitivity.

2. Discussion of Background

Mammography, along with physical examination, is the current procedure of choice for breast cancer screening. Screening mammography has been responsible for an estimated 30 to 35 percent reduction in breast cancer mortality rates. However, in 1996 approximately 185,700 new breast cancer cases were diagnosed and 44,300 women died from this disease. Women have about a 1 in 8 chance of being diagnosed with breast cancer, and 1 in 30 will die of this disease in her lifetime.

Although mammography is a well-studied and standardized methodology, for 10 to 30 percent of women diagnosed with breast cancer, their mammograms were interpreted as negative. Additionally, only 10 to 20 percent of patients referred for biopsy based on mammographic findings prove to have cancer. Further, estimates indicate the malignancies missed by radiologists are evident in two-thirds of the mammograms retrospectively. Missed detections may be attributed to several factors including: poor image quality, improper patient positioning, inaccurate interpretation, fibroglandular tissue obscuration, subtle nature of radiographic findings, eye fatigue, or oversight.

To increase sensitivity, a double reading has been suggested. However, the growing increase in the number of screening mammograms makes this option unlikely. Alternatively, a computer-aided diagnosis (CAD or CADx) system may act as a "second reader" to assist the radiologist in detecting and diagnosing lesions. Several investigators have attempted to analyze mammographic abnormalities with digital computers. However, the known studies are believed to have achieved rates of true-positive detections versus false-positive detections that are undesirably low.

Microcalcifications represent an ideal target for automated detection because subtle microcalcifications are often the first and sometimes the only radiographic findings in early, curable breast cancers, yet individual microcalcifications in a suspicious cluster have a fairly limited range of radiographic appearances. Between 30 and 50 percent of breast carcinomas detected radiographically demonstrate microcalcifications on mammograms, and between 60 and 80 percent of breast carcinomas reveal microcalcifications upon microscopic examination. Any increase in the detection rate of microcalcifications by mammography will lead to f further improvements in its efficacy in the detection of early breast cancer.

Although the promise of CAD systems is to increase the ability of physicians to diagnose cancer, the problem is that all CAD systems fail to detect some regions of interest that could be found by a human interpreter. However, human interpreters also miss regions of interest that are subsequently shown to be indicators of cancers. Missing a region that is associated with a cancer is termed a false negative error while associating a normal region with a cancer is termed a false positive error.

It is not yet clear how CAD system outputs are to be incorporated by practicing radiologists into their mammographic analyses. No existing CAD system can claim to find all of the suspicious regions detected by an average radiologist, and they tend to have unacceptably high false positive error rates. However, CAD systems are capable of finding some suspicious regions that may be missed by radiologists.

SUMMARY OF THE INVENTION

Accordingly, an object of this invention is to provide a method and system for automated detection of clustered microcalcifications from digital mammograms.

These and other objects are achieved according to the invention by providing a novel method and system for automated detection of clustered microcalcifications from digital mammograms in which a digital mammogram is obtained, parameters necessary for cropping the digital mammogram image are optimized, the digital mammogram is cropped based on the optimized cropping parameters to select breast tissue for further analysis, parameters necessary for detecting clustered microcalcifications are optimized, and clustered microcalcifications in the cropped digital mammogram are detected based on the optimized clustered microcalcification detection parameters.

The detected clustered microcalcifications are then stored as a detections image, the detections image is processed for display, and a computer-aided detection image is produced for review by a radiologist.

The radiologist first reviews the original mammograms and reports a set of suspicious regions of interest, S1. A CAD system, or more particularly, the CAD system of the invention, operates on the original mammogram and reports a second set of suspicious detections or regions of interest, S2. The radiologist then examines the set S2, accepts or rejects members of S2 as suspicious, thus forming a third set of suspicious detections, S3, that is a subset of set S2. The radiologist then creates a fourth set of suspicious detections, S4, that is the union of sets S 1 and S2, for subsequent diagnostic workups. CAD system outputs are thereby incorporated with the radiologist's mammographic analysis in a way that optimizes the overall sensitivity of detecting true positive regions of interest.

Other objects and advantages of the invention will be apparent from the following description, the accompanying drawings and the appended claims.

BRIEF DESCRIPTION OF THE DRAWINGS

FIG. 12 is a schematic diagram illustrating a 3×3 cross-shaped median filter of the invention;

DETAILED DESCRIPTION OF THE PREFERRED EMBODIMENT

Figure 1:
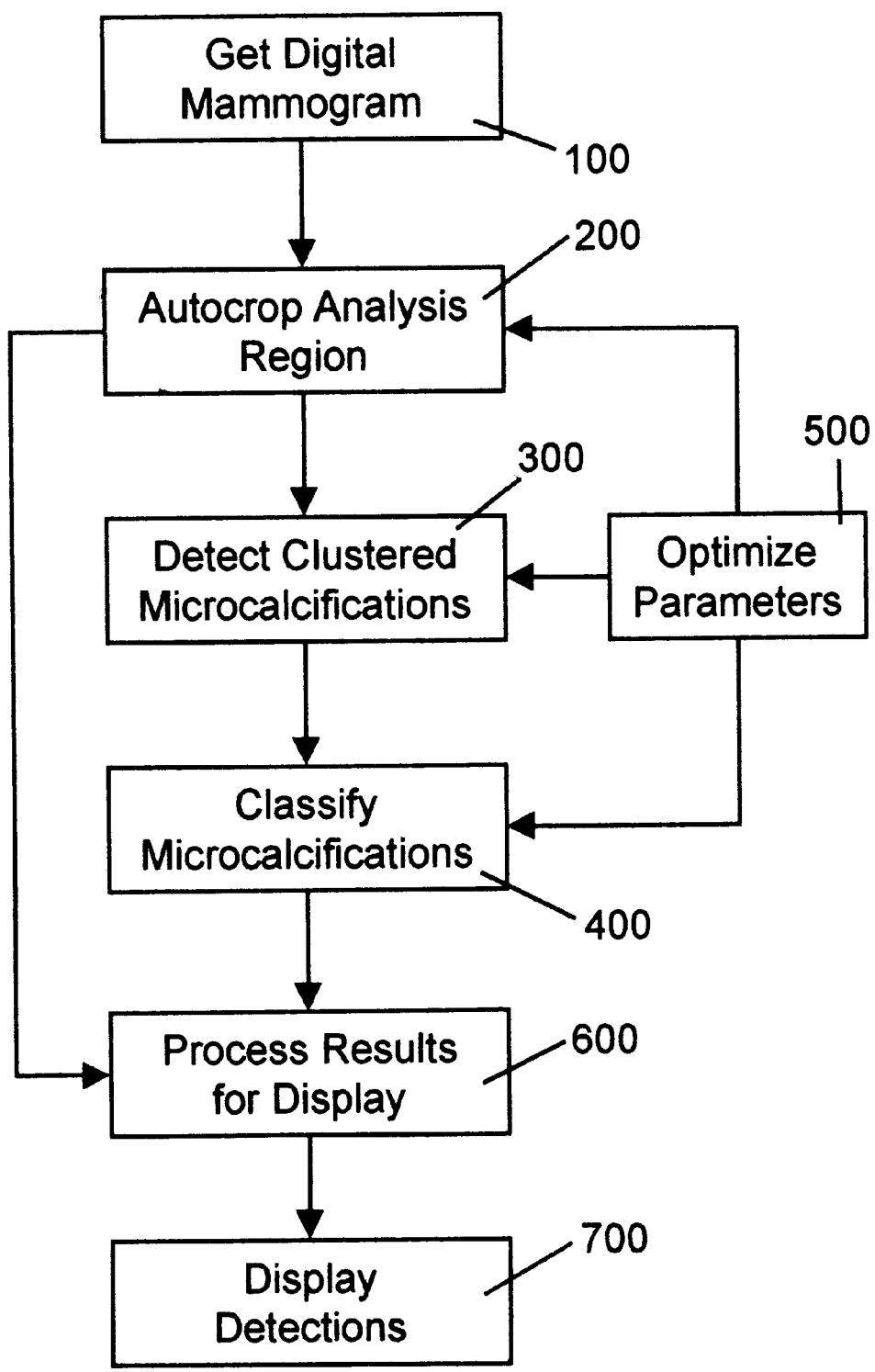
FIG. 1 is a flow diagram illustrating the automated system for the detection of clustered microcalcifications in a digital mammogram.

Referring now to the drawings, wherein like reference numerals designate identical or corresponding parts throughout the several views, and more particularly to FIG. 1 thereof, there is shown a flow diagram illustrating a sequence of steps performed in order to detect the locations of clusters of microcalcifications within a digital mammogram.

In a first step 100, a digital mammogram is obtained using hardware such as digital mammography systems, or by digitizing mammography films using laser or charge-coupled device (CCD) digitizers. In an optimized cropping step 200, a rectangular analysis region containing breast tissue is segmented from the digital mammogram image and a binary mask corresponding to the breast tissue is created or use in later processing steps to decrease the time required for processing the mammogram image. The binary mask is also used to limit detections to areas of the image containing breast tissue.

Clustered microcalcifications are detected in a clustered microcalcification detection step 300. After first filtering the cropped image with a median filter to reduce noise, the image is filtered using an optimized difference of Gaussians (DoG) filter to enhance the microcalcifications. The DoG-filtered image is then subjected to optimized threshold tests to detect potential microcalcifications. The detected microcalcifications are shrunk to single-pixel representations and detections outside of the breast area are removed. The remaining microcalcifications are grouped into clusters. Features are then computed for the clusters. Detected clusters are classified as either suspicious or non-suspicious in a classification step 400.

The parameters used by the autocropping, clustered microcalcification detection, and classification steps 200, 300, 400 are optimized in a parameter-optimizing step 500. The parameters are optimized by parameter-optimizing means that uses a genetic algorithm (GA) so as to maximize the true-positive detection rate while minimizing the false-positive detection rate. Of course, other optimization schemes may be used as well.

The detected clustered microcalcifications are stored in a list of image coordinates. The detection results are processed in a processing step 600 by simply adding an offset to each of the microcalcification coordinates to account for translation of the coordinates incurred as a result of the cropping procedure. Detected clustered microcalcifications are indicated on the digital mammogram by means of rectangles drawn around the clustered microcalcifications in a display step 700. Other indicators may be used such as, for example, arrows pointing to suspected microcalcifications, or ellipses around suspected microcalcifications.

ACQUIRING A DIGITAL REPRESENTATION OF A MAMMOGRAM

One method of obtaining digital mammograms comprises digitizing radiologic films by means of a laser or charge-coupled device (CCD) scanner. Digital images obtained in this manner typically have a sample spacing of about 100 $\mu$m per pixel, with a gray-level resolution of 10 to 12 bits per pixel. In one embodiment of the present invention, radiologic films are scanned using a Model CX812T digitizer manufactured by Radiographic Digital Imaging of Compton, Calif., to produce digital images having 50 $\mu$m spacing per pixel and 12 bits of gray-level resolution per pixel. Another possible input source for digital images is a digital mammography unit from Trex Medical Corporation of Danbury, Conn., which has a spatial resolution of about 45 $\mu$m per pixel and a gray-level resolution of 14 bits per pixel.

The digital images are stored as digital representations of the original mammogram images on computer-readable storage media. In a preferred embodiment, the digital representations or images are stored on a 2 GB hard drive of a general-purpose computer such as a PC having dual Pentium II® microprocessors running at 200 MHZ, 512 MB of RAM memory, a ViewSonic PT813® monitor, a pointing device, and a Lexmark Optra S1625® printer. The system operates within a Windows NT® operating system.

AUTOCROPPING

Figure 2:
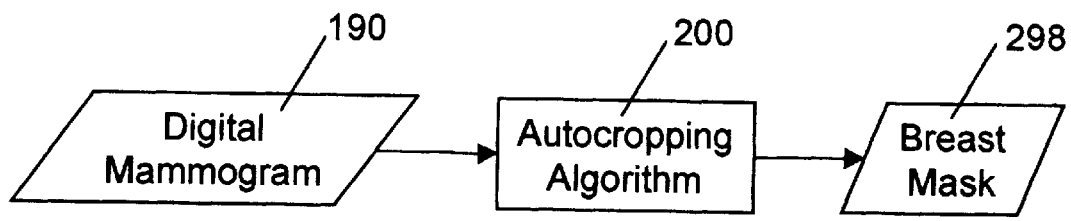
FIGS. 2 and 3 are flow diagrams illustrating the autocropping method and system of the invention.
Figure 3:
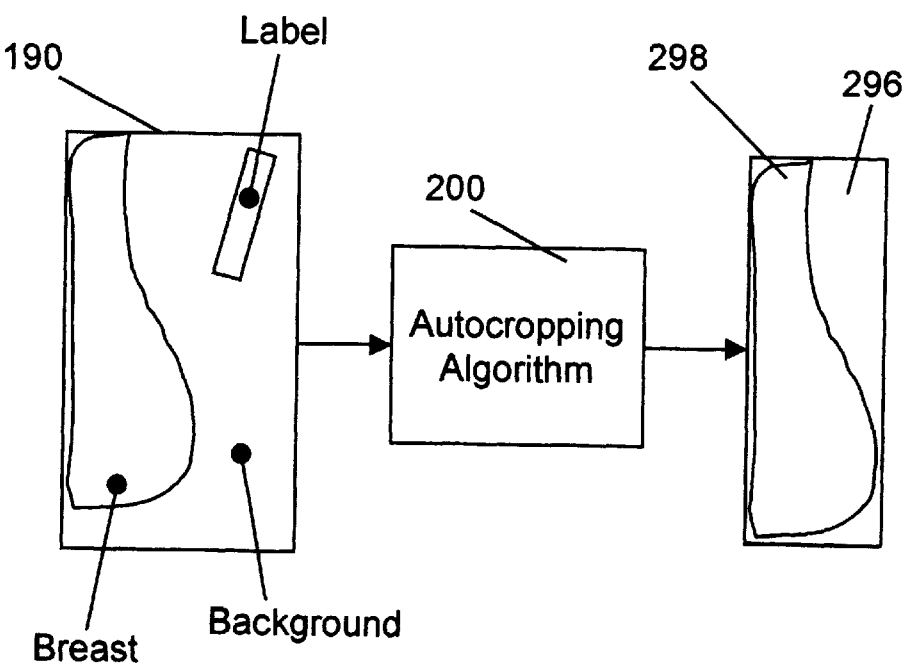
Figure 4:
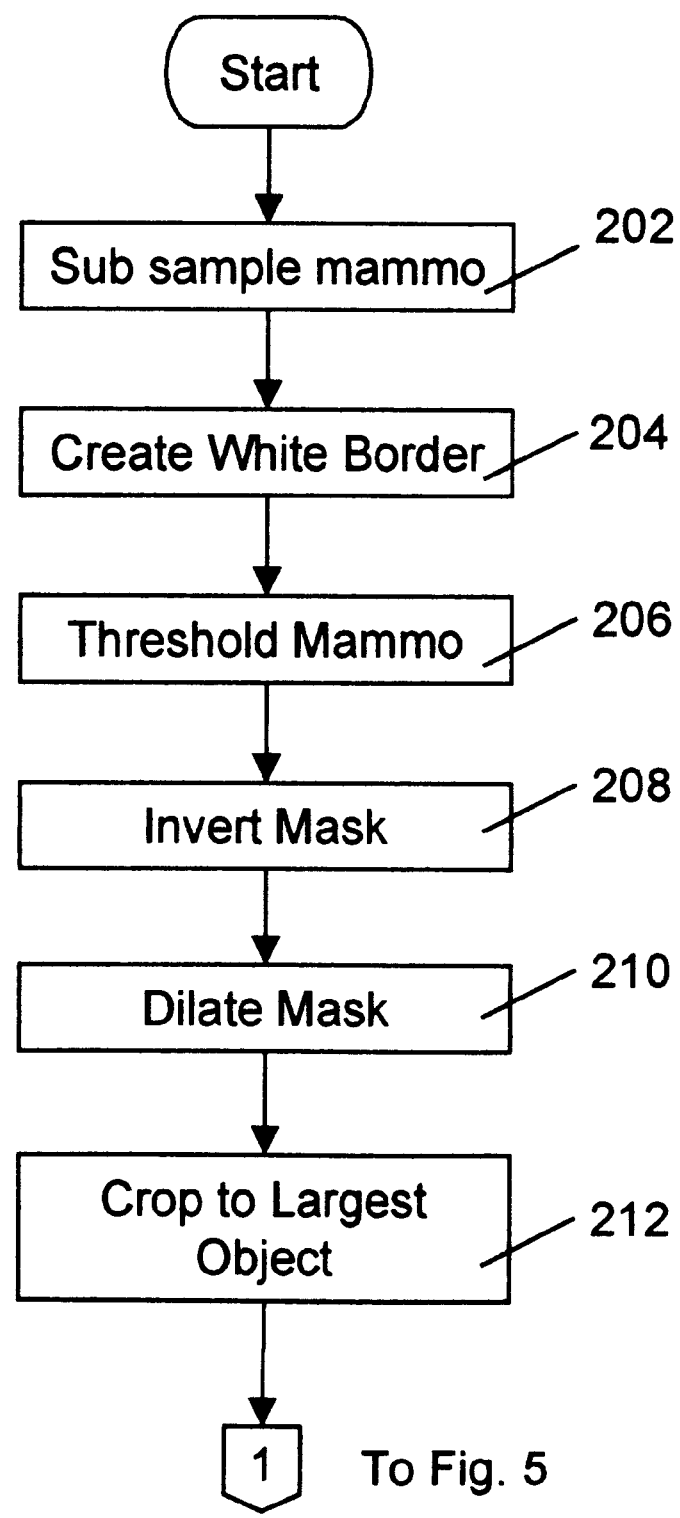
FIGS. 4–10 are flow diagrams illustrating in more detail the autocropping method and system of the invention.
Figure 5:
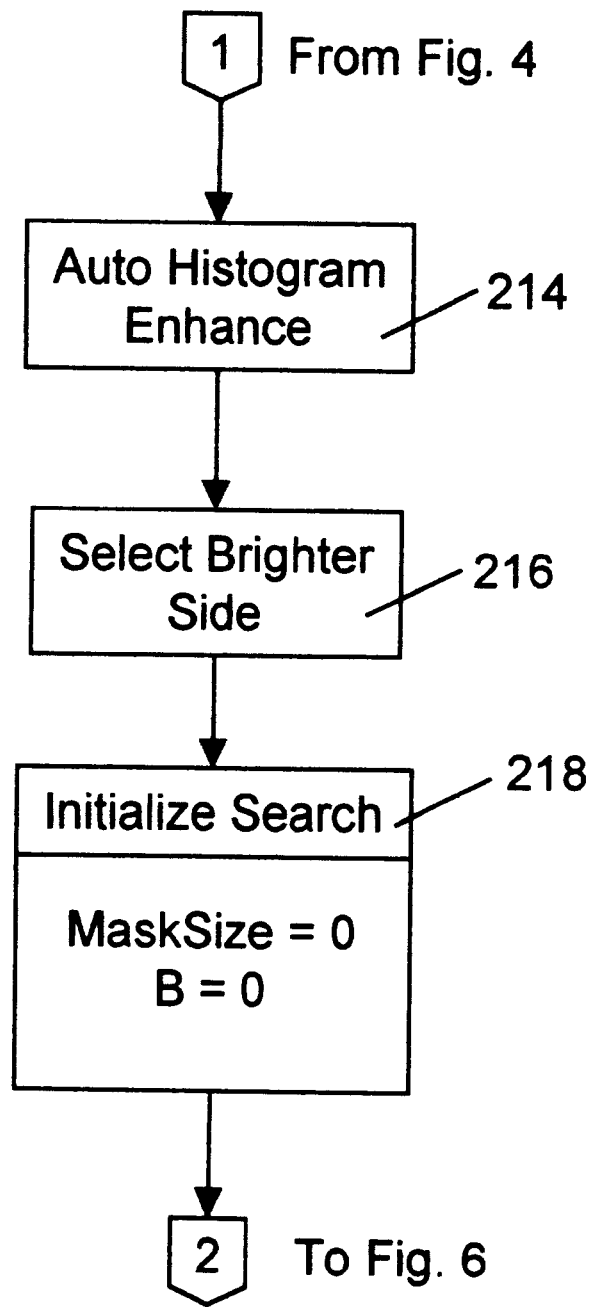
Figure 6:
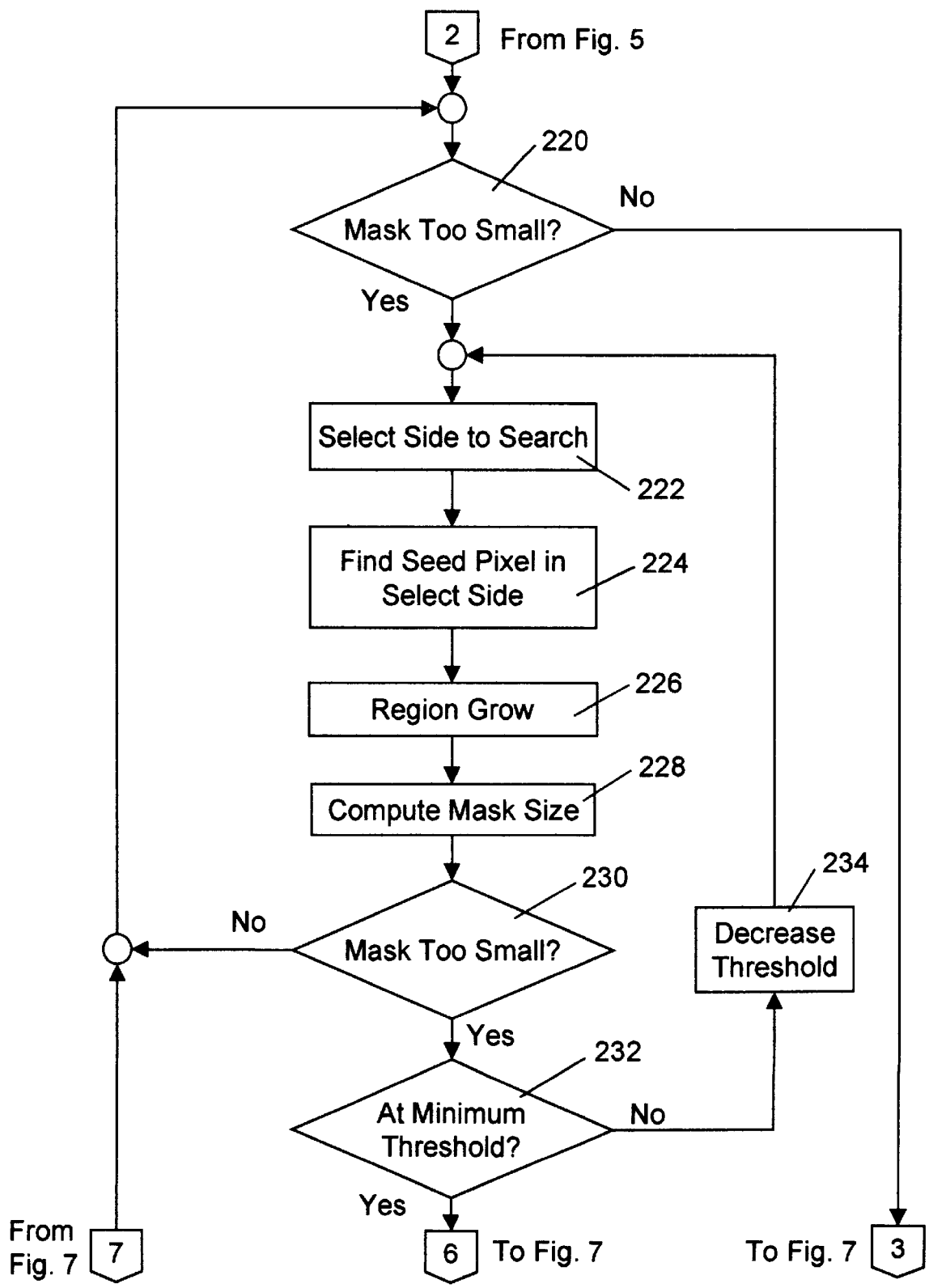
Figure 7:
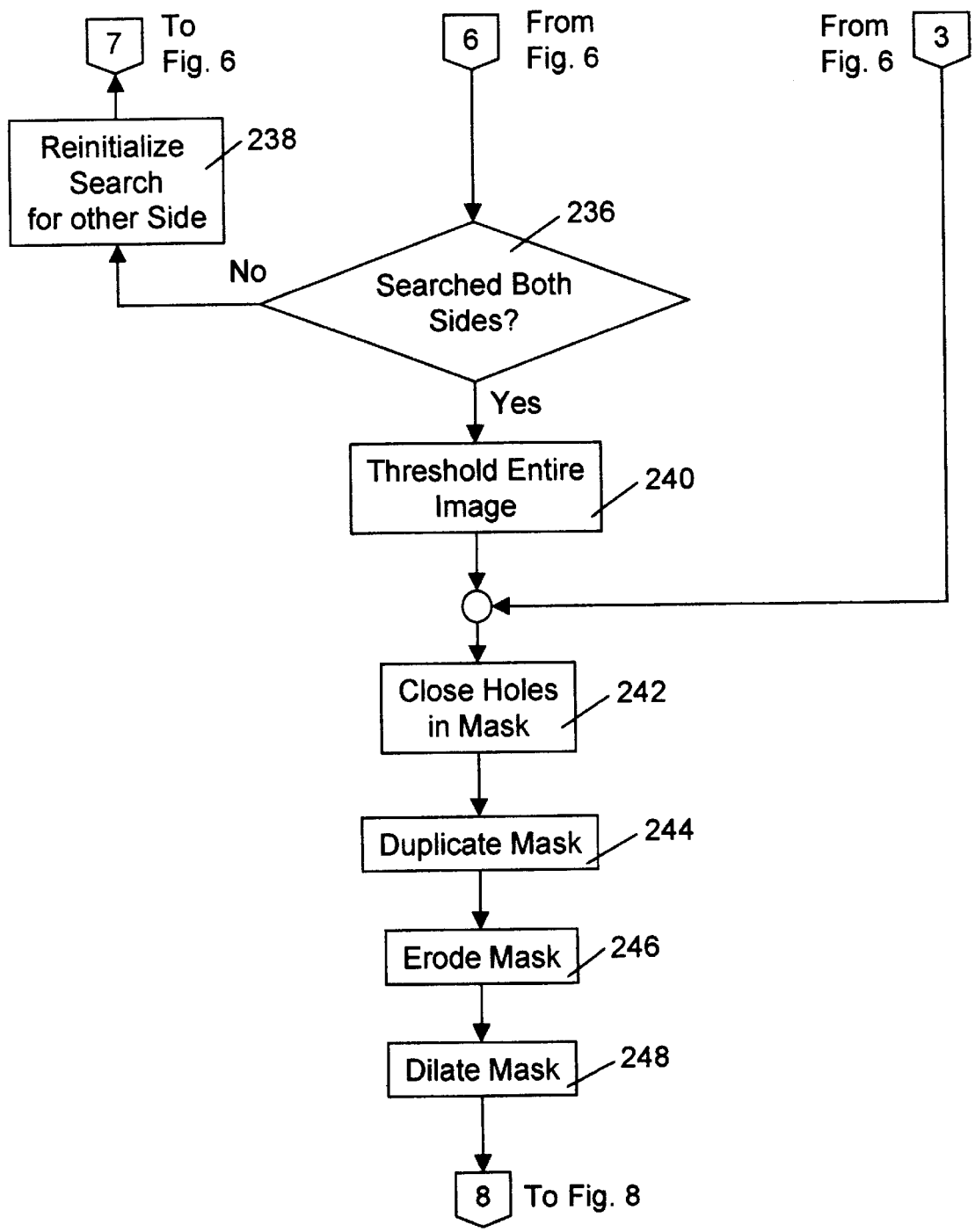
Figure 8:
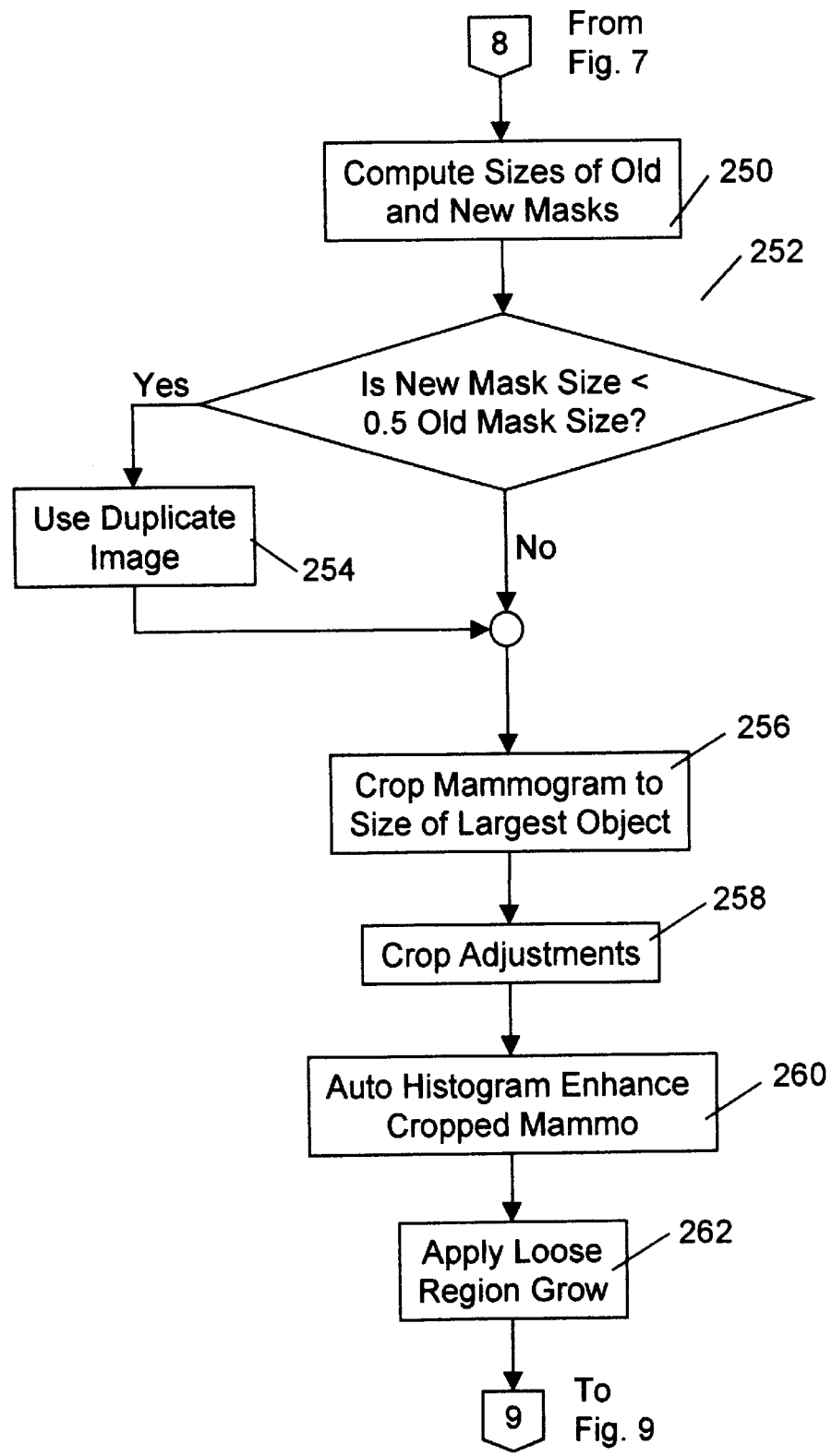
Figure 9:
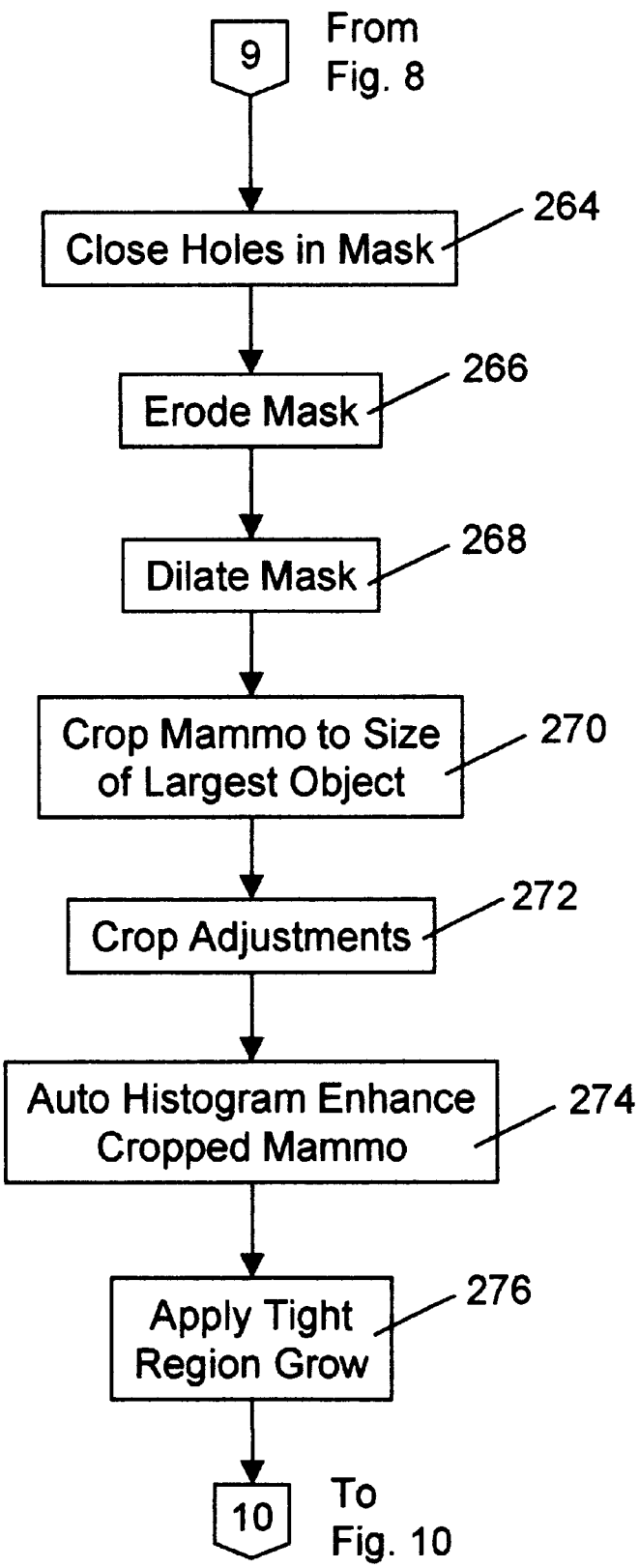
Figure 10:
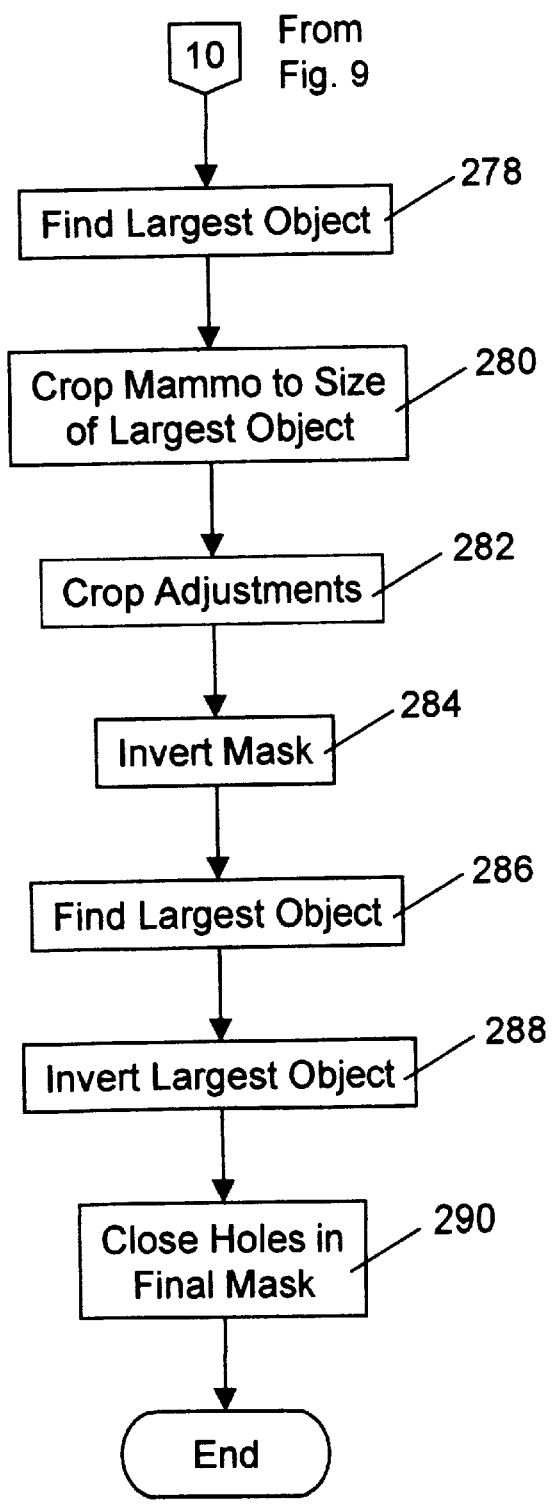

As may be seen in FIGS. 2 and 3, a digital mammogram image 190 is first cropped to segment an analysis region 296 from the image and produce a binary mask 298 corresponding to breast tissue in the analysis region. Preferably, the cropping is performed automatically, although it could be cropped manually. The image is cropped as a preliminary step because the breast tissue does not cover the whole radiographic film. Focusing the processing of the image on only that portion of the image which contains breast tissue reduces the time required to process the image. Also, other items appearing on the film, such as labels and patient information, are excluded from consideration, and false-positive indications lying outside of the breast tissue area are eliminated.

Referring to FIGS. 4 through 10, the autocropping process will be described in detail. The image is first subsampled from 50 μm to 400 μm to reduce the amount of data to be processed in step 202. Of course, the image may be down-sampled to other resolutions as desired. Not all of the original image data is needed to reliably segment the breast tissue from the remainder of the image. Subsampling every eighth pixel in both the horizontal and vertical directions reduces the amount of data by 64 times. For purposes of segmenting the breast tissue from the rest of the image, the consequent loss of resolution is immaterial.

A white border twenty pixels in width is added around all sides of the subsampled image in step 204. White corresponds to the maximum pixel value possible given the number of bits used to represent each pixel. For images having 12 bits of gray-scale resolution, the maximum gray-scale value is 4095. The bordered image is then thresholded in step 206 with a relatively high threshold value such that most of the breast tissue is guaranteed to be less than the threshold to produce a binary image. In one embodiment of the invention, the threshold is set equal to a predetermined percentage of the gray-scale value of a pixel near the top middle portion of the image. The thresholded image is then inverted, that is, ones become zeroes and zeroes become ones, in step 208. The inverted image is then dilated in step 210. Dilation is a morphological operation in which each pixel in a binary image is turned on, that is, set to a value of one, if any of its neighboring pixels are on. If the pixel is already on, it is left on.

In step 212 the dilated image is cropped to the size of the largest blob. Blobs are contiguous groups of pixels having the value one. This step 212 removes bright borders from the subsampled mammogram representation while ensuring that none of the breast area is reduced. Other techniques that threshold to find the border have a very difficult time dealing with bright areas in the breast adjacent to the border such as, for example, when breast implants are visible in the image. Pixels from the original image, resulting from step 202, corresponding to the locations of the pixels in the cropped blob, are selected for subsequent processing. Note that this is a simple subset of pixels from the input image.

The image from step 212 is histogram equalized in step 214. The average brightness of the image will vary widely from mammogram to mammogram. Moreover, different digitizers having different optical density characteristics are an additional source of variability in brightness levels in the digital representation of the mammogram. The breast mask that is the output of the autocropper is mainly defined by means of a region-growing algorithm that requires a single contrast setting to work properly. However, it has been determined experimentally that a single contrast setting will not work for a wide range of image inputs. Therefore, each image is mapped into a normalized image space using an automatic histogram enhancement process, after which a single contrast setting works well.

First, a histogram of the image is obtained. Typically, most of the data in the breast area will be in the lower histogram bins (corresponding to gray-scale values of about 0–1000), with borders and labels being in the higher bins (corresponding to gray-scale values of about 4000–4095) for 12-bit data. The upper and lower bin values that contain the typical breast data are determined. The lower bin value is the first highest peak encountered when going from the lowest gray-scale value toward the highest gray-scale value. The upper bin is the last zero-value bin encountered when going from the highest gray-scale level toward the lowest gray-scale value. Then the data are reduced to an eight-bit representation and linearly stretched over the range of the data type. For example, values in the lower bins are set to zero. Values of data in the upper bins are set to 255. The rest of the data are then linearly mapped between the lower and upper bins.

After the image has been histogram equalized, the equalized image may be considered to be a matrix. The image matrix is divided into left and right halves, of equal size if possible, and the brighter side is selected in a step 216. The sums of all the pixels in the left and right halves are computed. The sum values are then compared and the side having the greater sum is the brighter side.

Prior to region growing the brighter side, algorithm variables are initialized in step 218. The size of the region-grown mask is preliminarily checked in step 220. If it is large enough, then the mask is acceptable. Otherwise, processing continues to find the mask. The side of the image to be region grown is selected in step 222. In step 224 this region is searched to find its maximum gray-scale value. This maximum value is used to find a pixel to start a region-growing algorithm. Region growing is the process of grouping connected pixels sharing some like characteristic. The choice of characteristic influences the resultant region. The input to a region growing function is a gray-scale image and a starting point to begin growing. The output is a binary image with ones indicating pixels within the grown region, i.e., blobs. Region growing will create a single blob, but that blob may have within it internal holes, that is, pixels that are off. To grow a blob, each of the four nearest neighbors of a pixel of interest are looked at. The contrast ratio is computed for each nearest neighbor pixel. If the contrast ratio is less than a contrast ratio threshold, then the neighbor pixel is set to a one in a binary mask image. Otherwise, the neighbor pixel is set to zero. The region growing algorithm spirals outwardly from the starting or seed pixel, progressively looking at nearest neighbor pixels until done. To those skilled in the art, it is clear that other region growing algorithms may also be applied.

In step 226, region growing begins with the pixel identified from the previous step 224 to produce a binary mask. The size of the mask resulting from step 226 is computed in step 228 and checked in step 230. There may be three points of failure for this approach. First, the brightest point in the search region may be an artifact outside the breast. Therefore, if the resulting mask is not large enough (50 pixels), then the search region is moved closer to the side of the image and searched again. This is repeated three times, each time lowering the contrast value threshold. This corresponds to the path taken through steps 232 and 234. Second, the side selection approach may be in error. Therefore, if a valid breast mask is not found in the first side searched, then the other side of the equalized image is searched. This corresponds to the path taken through steps 236 and 238. Third, if a valid breast mask is not found on either side, then the whole breast is thresholded and the largest object is taken to be the breast mask in step 240.

Since a constant contrast value is used in the region-growing algorithm, some masks will be too large. Typically, there will be "tails" along the edge of the digitized mammogram image where extra light leaked in while the original mammogram film was being digitized. The tails are reduced by applying a series of erodes and then a series of dilates to the image. Erosion is a morphological operation in which each pixel in a binary image is turned off unless all of its neighbors are on. If the pixel is already off, it is left off. But first, the holes in the mask must be filled in or the multiple erodes may break the mask into disjoint sections. Thus, holes in the mask are closed in step 242 by means of a majority operation. The majority operation is a morphological operation in which each pixel in a binary image is turned on if a majority of its neighboring pixels are on. If the pixel is already on, it is left on.

However, another problem is that some smaller breast masks can not undergo as many erodes as can larger breast masks. Therefore, as a fail-safe measure, the sum of the breast mask is taken before and after the erodes and dilates. If the size is reduced too much (i.e., by more than 50%), the original mask before the morphological operators is used. Thus, a duplicate copy of the mask is made in step 244 before the mask is eroded and dilated in steps 246 and 248, respectively. The size of the resultant mask is then computed in step 250 and compared with the size of the mask from step 242 in step 252. If the new size is less than half the old size, then the duplicate mask, from step 244, is selected in step 254 for subsequent processing. Otherwise, the resultant mask from step 248 is used.

The original image (from step 202) is then cropped to the size of the breast mask just found (either from step 242 or step 248) in step 256. In case the resulting mask is too small for subsequent processing, a crop adjustment is always made in step 258. The adjustment comes in the form of increasing the size of the breast mask bounding box by including additional pixels from the original image in the cropped image.

The cropped image is then automatically histogram enhanced in step 260 as previously described above in connection with step 214. This enhanced image is passed through a loose region growing step 262 to produce a generous mask. This means that the image is subjected to a lower threshold to yield more "on" pixels. This mask is then subjected to hole-closing, eroding, and dilating in steps 264, 266, and 268, respectively, as above, but to a lesser degree.

The same steps described above are repeated one final time in steps 270 through 276, but the crop adjustments are less and the contrast value is increased for a tight region growing step 276. This tight region growing step 276 can afford the higher contrast value since it will be region growing in just the cropped image. This results in a parsimonious estimate of breast tissue. The resulting mask is segmented to find the largest object in step 278 and its bounding box shrunk to just enclose the object in step 280. There may still be some holes in the breast mask. Therefore, after crop adjustments in step 282, the mask is inverted in step 284 and the largest object is found in step 286. This largest object is extracted and then inverted in step 288 to obtain the penultimate mask.

The final mask is obtained by closing holes in the penultimate mask with multiple majority operations and dilations in step 290. The image is then cropped to the size of the resulting mask and the autocropping is complete. An important result from the autocropper is the offset of the cropped image. This is the pixel location in the original image that corresponds to the pixel in the upper left pixel of the cropped image. Keeping track of all the cropping and crop adjustments determines this offset value.

The output of the autocropping process is a rectangular array of pixels representing a binary mask wherein the pixels corresponding to breast tissue are assigned a value of one while the remainder of the pixels are assigned a value of zero. Put another way, the binary mask is a silhouette of the breast made up of ones while the background is made up of zeroes.

Parameters of the autocropper may be optimized to obtain better breast masks. The procedure is described below in the optimization section.

DETECTION OF CLUSTERED MICROCALCIFICATIONS

Figure 11:
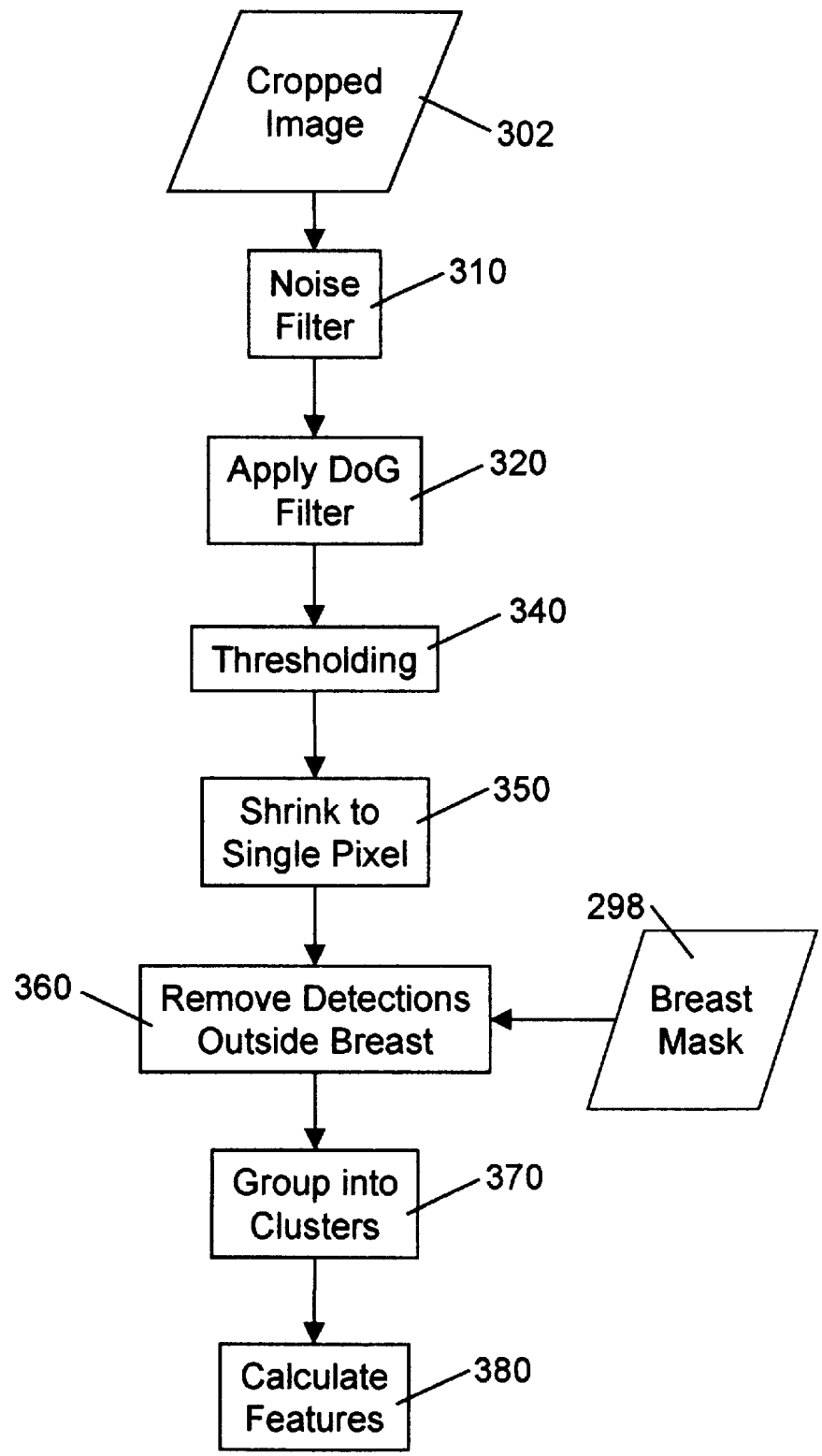
FIG. 11 is a flow diagram illustrating in greater detail the clustered microcalcification detector of the invention.

Turning now to FIG. 11, there is seen therein a flow diagram illustrating in greater detail the clustered microcalcification detection system 300 of the invention.

That portion of the digital representation of the mammogram corresponding to the analysis region 296, designated a cropped sub-image 302, produced in the cropping step 200, is first processed to reduce noise in a noise reduction step 310 to reduce digitization noise that contributes to false detections of microcalcifications. The noise-reduced image is then filtered using an optimized target-size-dependent difference of Gaussians (DoG) spatial kernel in step 320 to enhance differences between targets and background, thus creating global and local maxima in the filtered image. The optimized DoG-filtered image is then thresholded in step 340 to segment maxima that represent potential detections of micro calcifications.

The detected maxima are converted to single-pixel coordinate representations in a conversion step 350. The coordinate representations of the detected maxima are compared with the binary mask of the analysis area in a first false-positive removal step 360 to remove false detections outside the breast mask area. The remaining coordinate representations in the analysis area are clustered in a clustering step 370. Features are computed for the remaining clusters in a feature computation step 380 and used to remove non-suspicious detections in a classifying step 400 (FIG. 1). The remaining detections are outputted as detected clustered microcalcifications in an outputting step 600 in the form of cluster coordinates.

Figure 12:
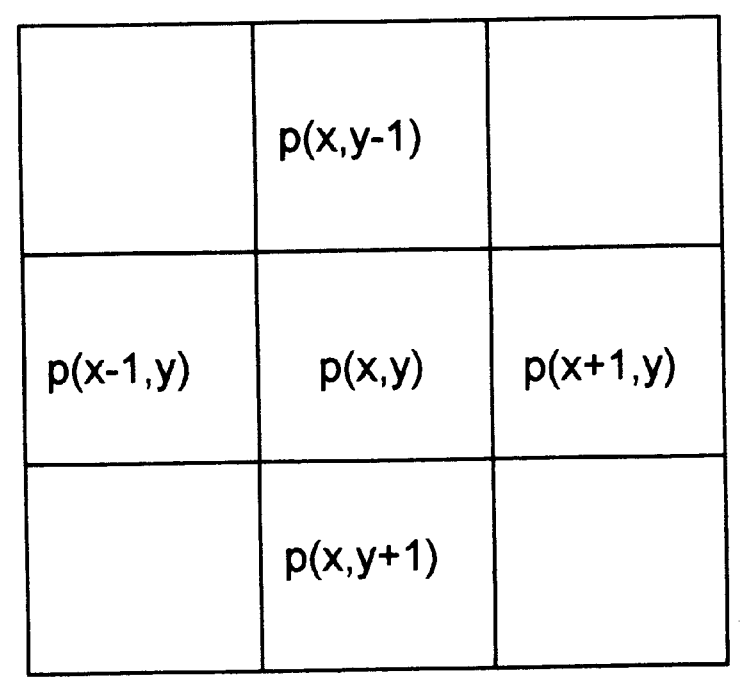

Turning now to a more detailed discussion of the steps in the clustered microcalcification detection process, the digital mammogram image is first filtered to reduce noise in the image. Although the main limitation in image quality should be the granularity of the film emulsion, noise is introduced from the process of digitization. This noise may later be detected as a pseudocalcification. In this system, a cross-shaped median filter is used because it is well known to be extremely effective at removing single-pixel noise. The median filter is a non-linear spatial filter that replaces each pixel value with the median of the pixel values within a kernel of chosen size and shape centered at a pixel of interest. Referring to FIG. 12, it may be seen that the cross shape is formed by the set of pixels which include the center pixel and its four nearest neighbors. The cross shape preserves lines and corners better than typical block-shaped median filters and limits the possible substitution to the four nearest neighbors, thereby reducing the potential for edge displacement.

After noise has been reduced, the image is filtered with an optimized DoG kernel to enhance microcalcifications. Filtering is accomplished by convolving the noise-reduced image with the DoG kernel. In an alternative embodiment, filtering is accomplished by first obtaining the fast Fourier transforms (FFTs) of the noise-reduced image and the DoG kernel, then multiplying the FFTs together, and taking the inverse FFT of the result.

The DoG kernel was chosen because neurophysiological experiments provide evidence that the human visual pathway includes a set of "channels" that are spatial frequency selective. Essentially, at each point in the visual field, there are size-tuned filters or masks analyzing an image. The operation of these spatial receptive fields can be approximated closely by a DoG.

The 2-D Gaussian mask is given as:

$$G(x, y) = ce^{\frac{-(x^2+y^2)}{2\sigma^2}} \quad (1)$$

where c normalizes the sum of mask elements to unity, x and y are horizontal and vertical indices, and σ is the standard deviation. Using Equation 1, the difference of two Gaussians with different σ yields:

$$DoG(x, y) = c_1 e^{\frac{-(x^2+y^2)}{2\sigma_1^2}} - c_2 e^{\frac{-(x^2+y^2)}{2\sigma_2^2}} \quad (2)$$

It has been shown that when $\sigma_2 = 1.6 \sigma_1$, then the DoG filter's response closely matches the response of human spatial receptive filters. Therefore, with motivation from human physiology, let the ratio of the DoG standard deviation constants be 1:1.6. Then, for a target of size (average width) t pixels, use $\sigma_2 = t/2$ and, from the rule of thumb, $\sigma_1 = \sigma_2/1.6$.

Figure 13:
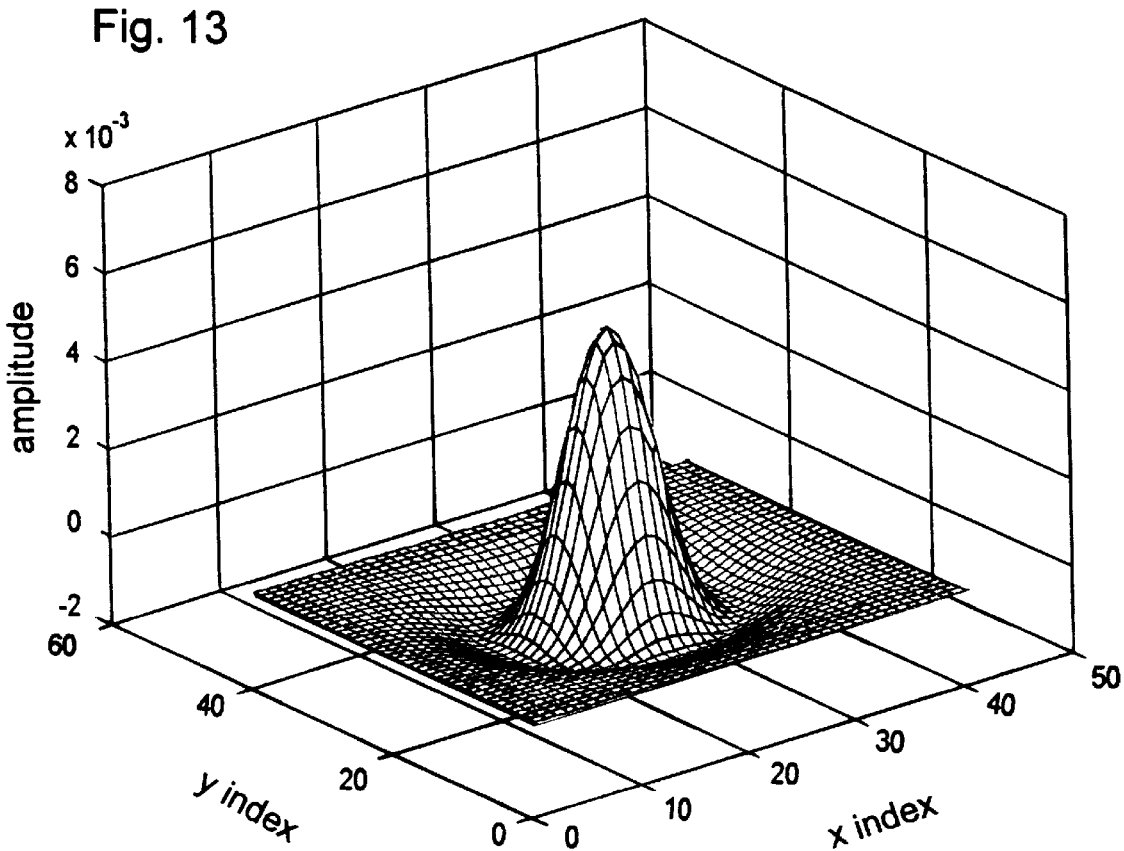
FIG. 13 is a three-dimensional plot of a Difference of Gaussians (DoG) filter kernel.
Figure 14:
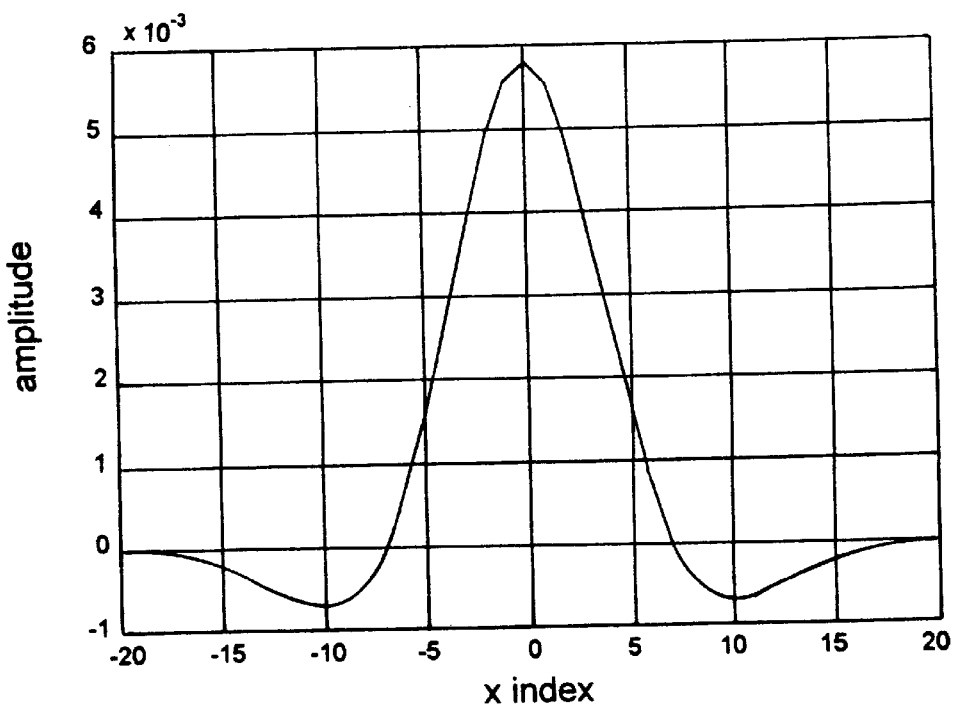
FIG. 14 is a cross-sectional view through the center of the DoG filter kernel of FIG. 13.

Since microcalcifications typically range from 100 to 300 μm in diameter, potential target sizes for the 50 μm digitized mammograms correspond to 2 to 6 pixels. It has been found that a DoG kernel constructed using an optimization technique for selecting the target size parameter, such as the GA detailed below, has an optimized target size of t=6.01 pixels. The targetsize t will vary depending on such factors as the resolution and scale of the image to be processed. The impulse response of a DoG filter having t=6.01 pixels and $\sigma_2 = 1.6 \sigma_1$, is shown in FIGS. 13 and 14.

Once the noised-reduced cropped image has been DoG filtered to enhance differences between targets and background, the DoG-filtered subimage contains differences in gray levels between potential microcalcifications and background. Although microcalcifications tend to be among the brightest objects in DoG-filtered subimages, they may exist within regions of high average gray levels and thus prove difficult to reliably segment. The thresholding process used in one embodiment of the invention that generally addresses these concerns involves pair-wise pixel "ANDing" of the results of global histogram and locally adaptive thresholding. However, the preferred embodiment of the invention uses sloping local thresholding.

Figure 15:
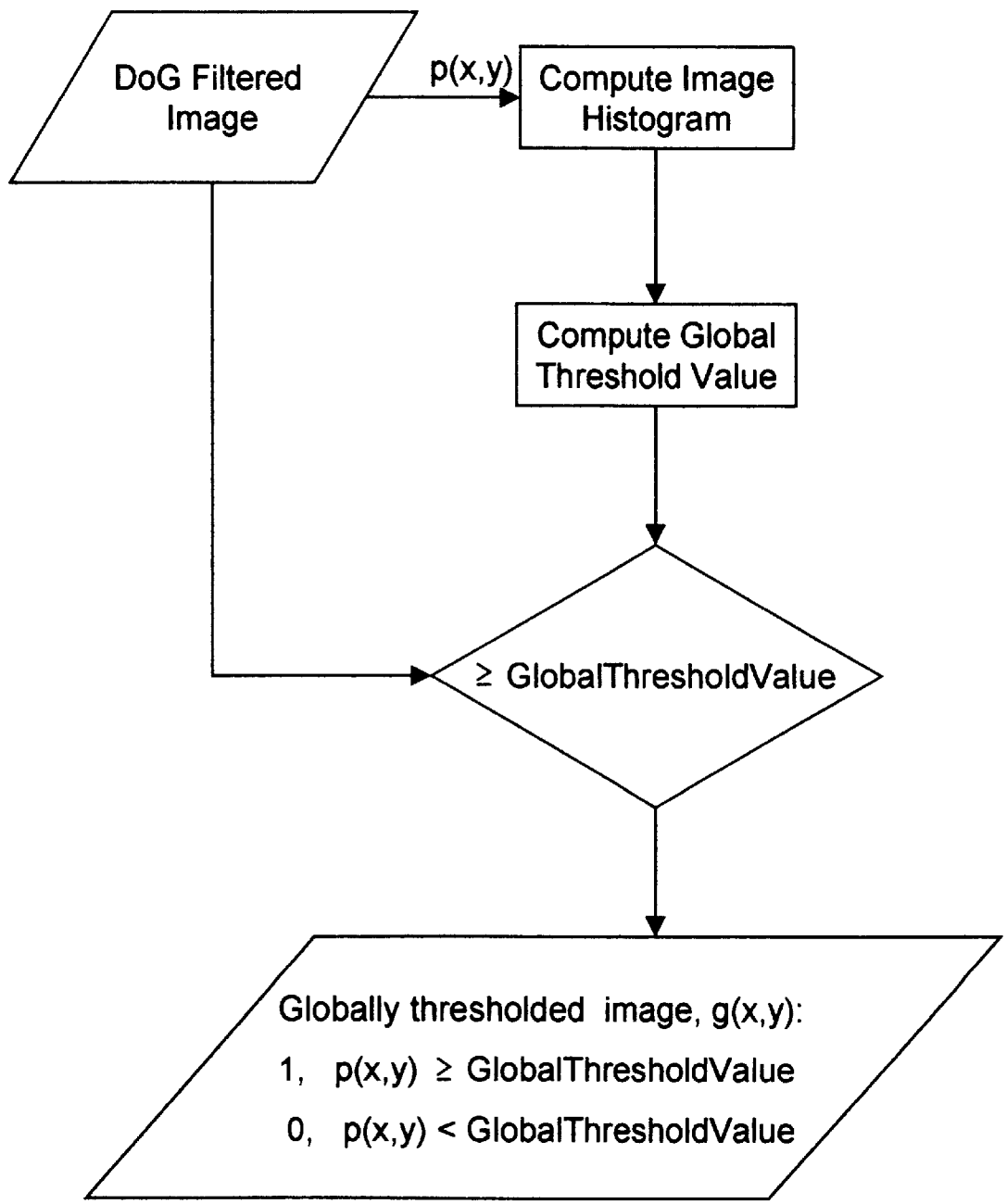
FIG. 15 is a flow diagram illustrating the global thresholding portion of the microcalcification detection system.
Figure 16:
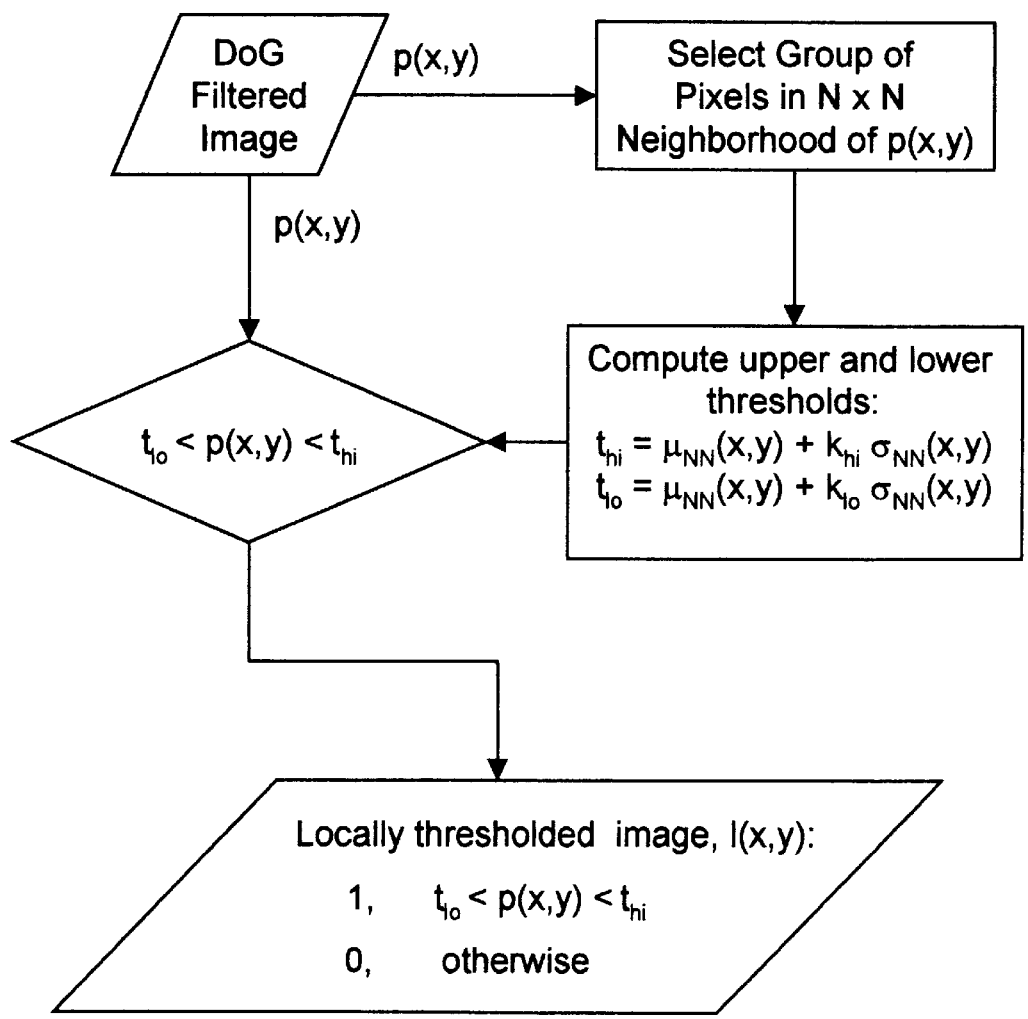
FIG. 16 is a flow diagram illustrating the dual local thresholding of the invention.

Since targets tend to exist within an image's higher gray levels, then the global threshold may be approximated by finding the level which segments a preselected percentage of the corresponding higher pixel levels in the image histogram. An embodiment of a global thresholding method is illustrated in FIG. 15. Locally adaptive thresholding may be implemented by varying the high and low thresholds based on the local pixel value mean and standard deviation. An embodiment of a dual-local thresholding method is illustrated in FIG. 16.

After computing the image histogram, $p(r_k)$, the gray level threshold, g, used to segment a preselected upper fraction, of the histogram, is found using:

$$f = 1 - \sum_{k=0}^{g} p(r_k) \quad (3)$$

where $r_k$ is the kit gray level, $0 \leq g \leq g_{max}$, and $g_{max}$ is the maximum gray level in the image.

Figure 17:
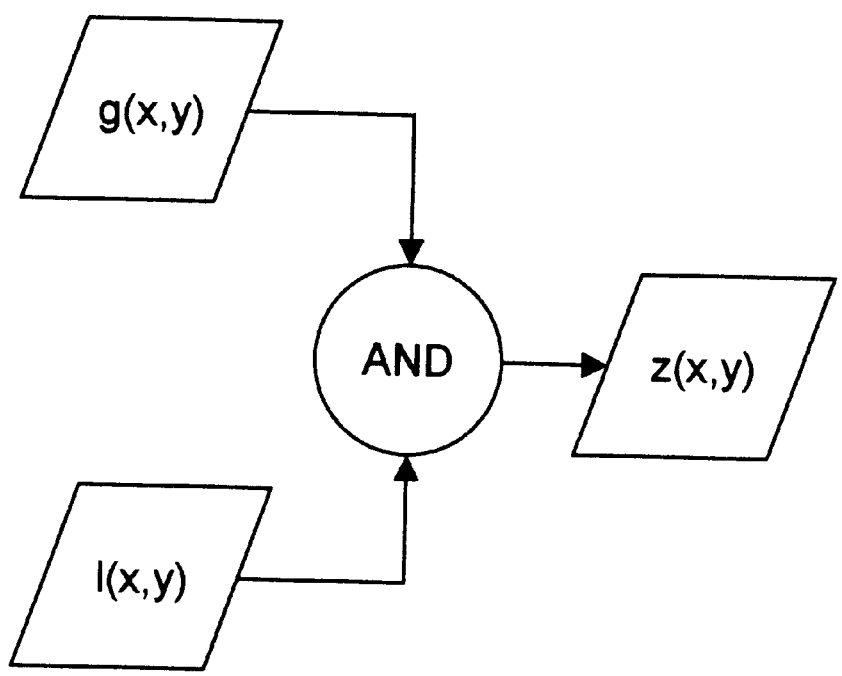
FIG. 17 is a flow diagram illustrating combining the results of global and dual-local thresholding.

The locally adaptive thresholds, $t_{lo}$ and $t_{hi}$, are found using $$t_{lo} = k_{lo}\sigma_{NN}(x,y) + \mu_{NN}(x,y) \quad (4)$$

and $$t_{hi} = k_{hi}\sigma_{NN}(x,y) + \mu_{NN}(x,y) \quad (5)$$

where $k_{lo}$ and $k_{hi}$ are used to preselect the multiple of $\sigma_{NN}(x,y)$, the local standard deviation of gray-level intensities, and $\mu_{NN}(x,y)$ is the local gray-level mean of the N×N neighborhood centered on the pixel at (x,y) of the DoG-filtered image. Other neighborhood shapes, such as rectangular, circular, and ellipsoidal, may also be used. Pixels whose brightness or gray-level value falls within the threshold interval, that is, $t_{lo}$<brightness<$t_{hi}$, are set equal to one. Optimization off, $k_{lo}$, $k_{hi}$, and N is discussed below in connection with the parameter-optimizing process. The results of the global thresholding process may be combined with the results of the local thresholding step by logically ANDing them as shown in FIG. 17. Alternatively, either thresholding method may be used alone.

Figure 18:
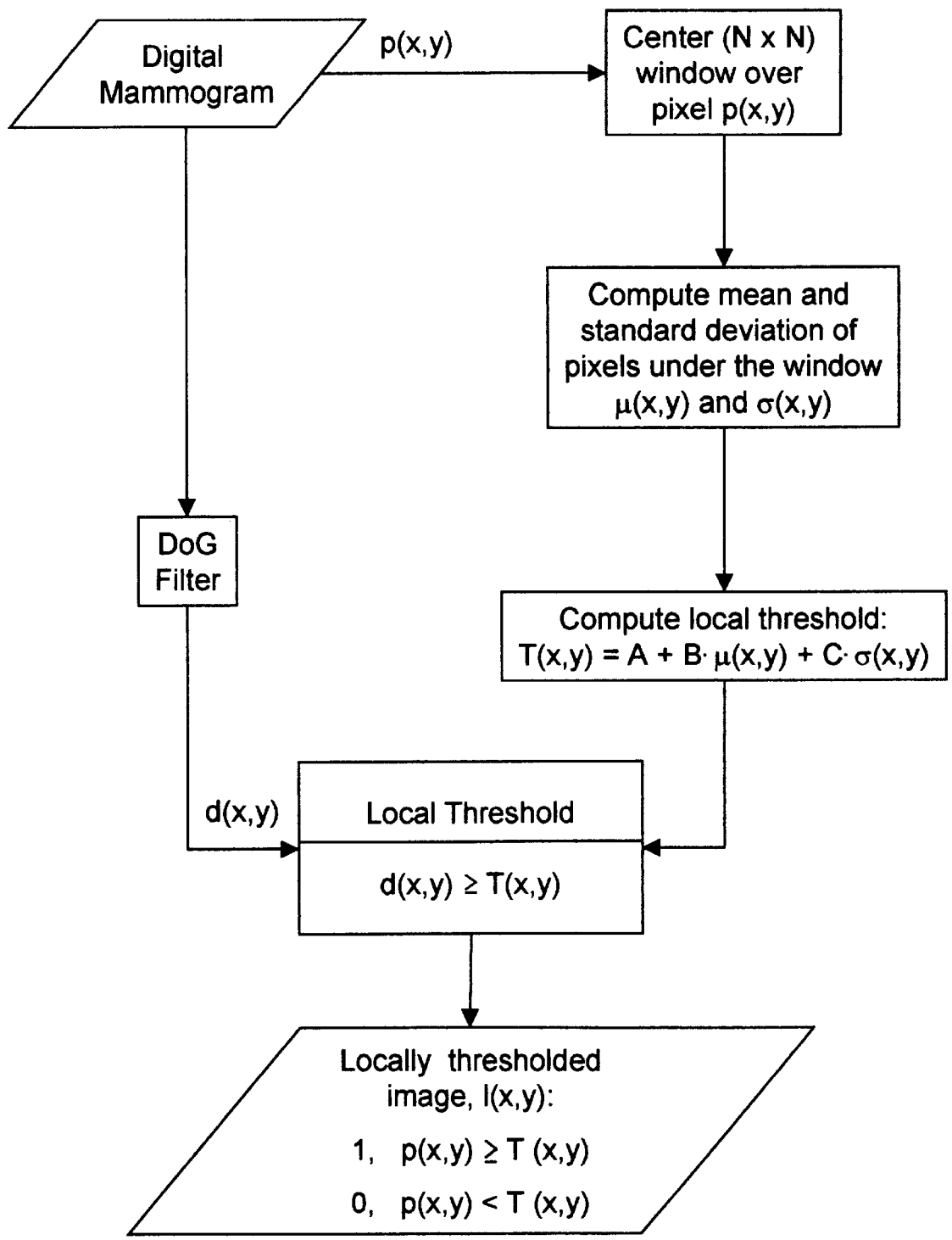
FIG. 18 is a flow diagram illustrating the sloping local thresholding of the invention.

The preferred thresholding means are illustrated in FIG. 18 wherein it may be seen that an N×N window is centered at a pixel x,y in the input image p(x,y). The mean, t(x,y), and standard deviation, σ(x,y), of the digital mammogram image pixels under the window are computed. A local threshold value, T(x,y), is computed as:

$$T(x,y) = A + B\mu(x,y) + C\sigma(x,y) \quad (6)$$

where values for N, A, B, and C are computed during a parameter optimization stage, discussed below. Values for T(x,y) are computed for every x,y location in the image.

The digital mammogram has also been DoG filtered, producing an image d(x,y). Each pixel of the DoG-filtered image d(x,y) is compared to the threshold value T(x,y). Pixels in the locally thresholded image $l_s(x,y)$ are set to one where values of the DoG-filtered image are greater than the threshold, and set to zero elsewhere.

The advantage of this novel local sloping thresholding method over prior art thresholding methods is that the threshold is computed from the pixels in a pre-DoG-filtered image rather than from a post-DoG-filtered image. This eliminates the need for background trend correction. In conventional local thresholding, the threshold is computed as:

$$T(x,y) = B\mu(x,y) + C\sigma(x,y) \quad (7)$$

from the mean and standard deviation of the DoG-filtered image. The problem of using a local threshold computed from the DoG-filtered image is that DoG-filtered images typically have mean values close to zero and standard deviations significantly affected by the presence of targets.

Local thresholds computed from the statistics of the DoG-filtered image suffer from the following adverse effects. First, since the mean value is close to zero, a degree of freedom is lost in the computation of the threshold, which becomes essentially a function of the standard deviation. Second, the absolute brightness of the input image is lost. To keep many spurious detections from occurring, it is desirable to have high thresholds in bright regions. However, the information about the local mean of the input image is not available in the DoG-filtered image. Finally, the standard deviations of DoG-filtered images are increased by detections of targets. This is so because when local bright spots of proper size exist in the original image, large gray-scale values result in the DoG-filtered image. Thus, the presence of targets in a region increases the local standard deviation thereby raising the threshold of that region. The higher threshold reduces the probability of passing a bright spot to subsequent processing stages.

The novel local thresholding method just described solves the above problems by computing thresholds from the input image, which are then applied to the DoG-filtered image. Additionally, the threshold computed here includes an offset term A, which is independent of the local image mean.

After thresholding, detections are converted to single-pixel representations by computing the centroid or center of gravity of groups of contiguous pixels found by the thresholding process. Detections are thus represented as single pixels having a value of logical one while the remaining pixels have a value of logical zero.

False-positive detections outside of the breast area are removed by logically ANDing the binary mask from the autocropper with the single-pixel representations of the detections.

Figure 19:
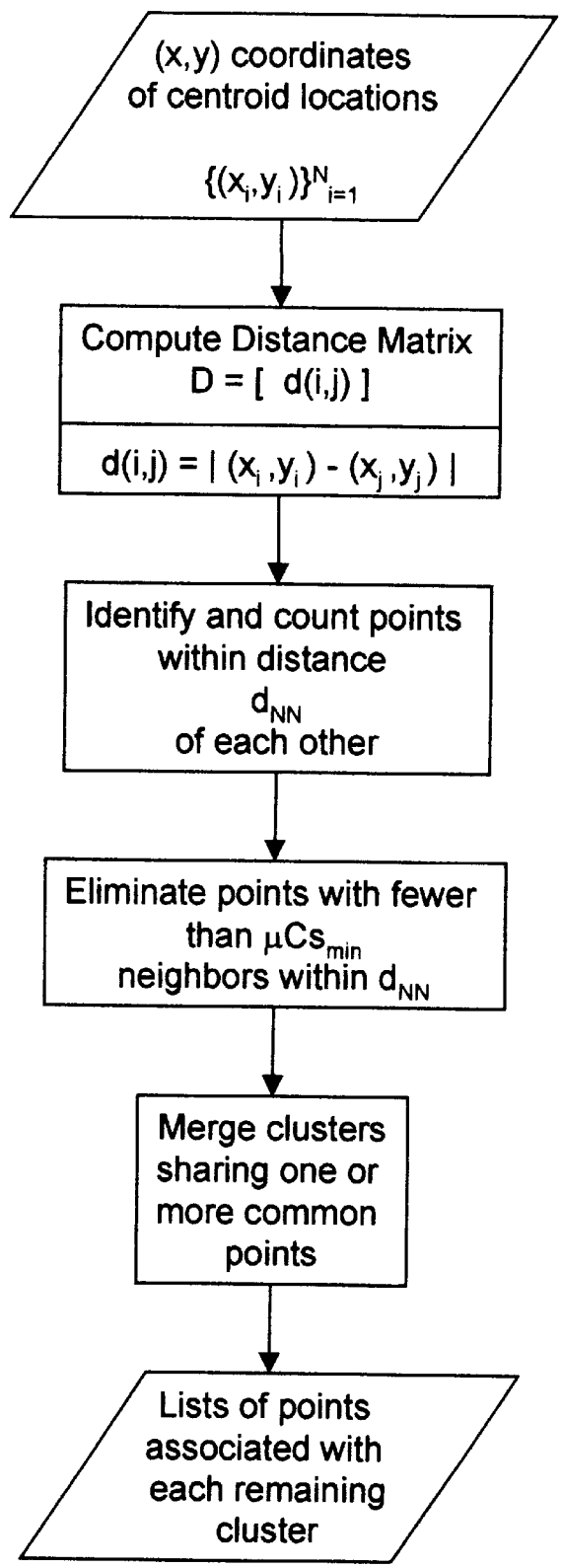
FIG. 19 is a flow diagram illustrating the clustering method of the invention.
Figure 20:
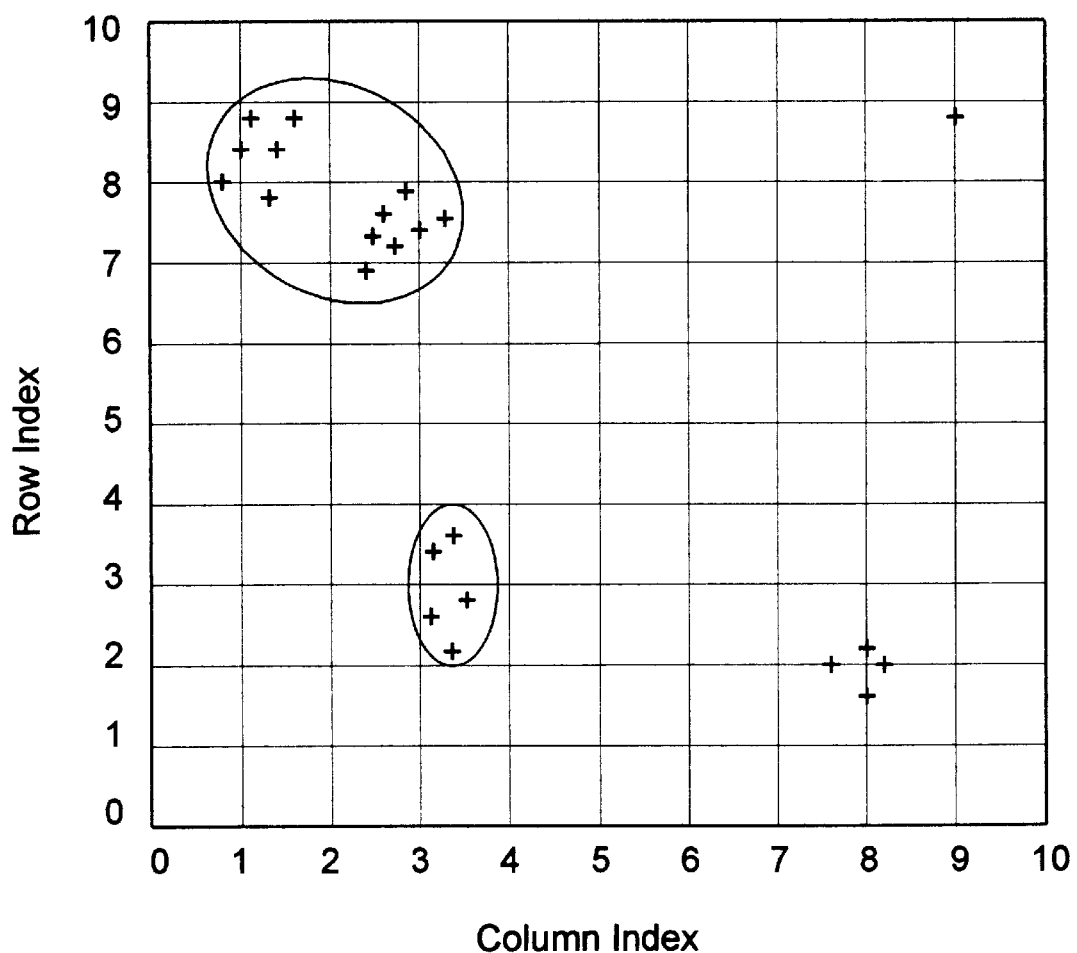
FIG. 20 is a schematic diagram illustrating the clustering method of the invention.

Calcifications associated with malignancies usually occur in clusters and can be extensive. The cluster detection module identifies clusters based on a clustering algorithm as depicted in FIG. 19. Specifically, a suspicious cluster is declared when at least $\mu Cs_{min}$ or more detected signals are separated by less than a nearest neighbor distance, $d_{nn}$. Optimization of $\mu Cs_{min}$ and $d_{nn}$ is discussed below in connection with the parameter optimizing process. FIG. 20 illustrates the clustering process for the case wherein $\mu Cs_{min}=5$ and $d_{nn}=4$.

Figure 21:
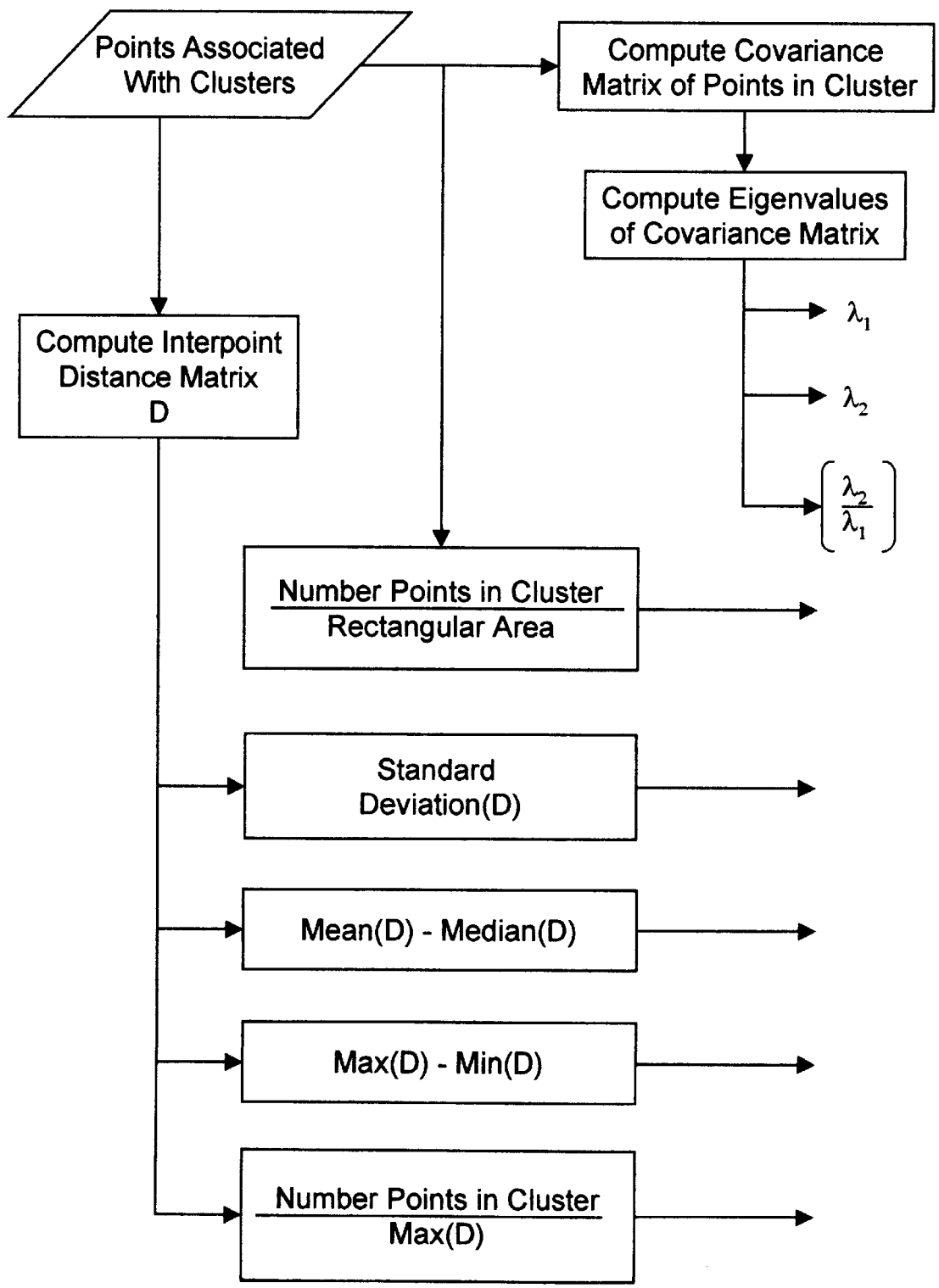
FIG. 21 is a flow diagram illustrating the feature computation process of the invention.

Additional false-positive clustered microcalcifications are removed by means of a classifier, detailed below. Features are extracted for each of the potential clustered microcalcifications as shown in FIG. 21. The eight features computed for each of the potential clustered microcalcifications in a preferred embodiment are:

1. The larger eigenvalue ($\lambda_1$) of the covariance matrix of the points in a cluster;
2. The smaller eigenvalue ($\lambda_2$) of the covariance matrix of the points in a cluster;
3. The ratio of the smaller eigenvalue of the covariance matrix to the larger eigenvalue of the covariance matrix of the points in a cluster. Equivalent to the ratio of the minor axis to the major axis of an ellipse fitted to cover the points in a cluster;
4. Linear density calculated as the number of detected microcalcifications divided by the maximum interpoint distance;
5. Standard deviation of the distances between points in a cluster;
6. Mean minus median of the distances between points in a cluster;
7. Range of points in cluster calculated as maximum interpoint distance minus the minimum interpoint distance; and
8. Density of a cluster calculated as the number of detections divided by the area of a box just large enough to enclose the detections.

Of course, other features could be computed for the potential microcalcification clusters, and the invention is not limited to the number or types of features enumerated herein.

CLASSIFYING DETECTIONS

The cluster features are provided as inputs to the classifier, which classifies each potential clustered microcalcification as either suspicious or not suspicious. In practice, the clustered microcalcification detector is only able to locate regions of interest in the digital representation of the original mammogram that may be associated with cancer. In any detector, there is a tradeoff between locating as many potentially suspicious regions as possible versus reducing the number of normal regions falsely detected as being potentially suspicious. CAD systems are designed to provide the largest detection rates possible at the expense of detecting potentially significant numbers of regions that are actually normal. Many of these unwanted detections are removed from consideration by applying pattern recognition techniques.

Pattern recognition is the process of making decisions based on measurements. In this system, regions of interest or detections are located by a detector, and then accepted or rejected for display. The first step in the process is to characterize the detected regions. Toward this end, multiple measurements are computed from each of the detected regions. Each measurement is referred to as a feature. A collection of measurements for a detected region is referred to as a feature vector, wherein each element of the vector represents a feature value. The feature vector is input to a discriminant function.

Figure 22:
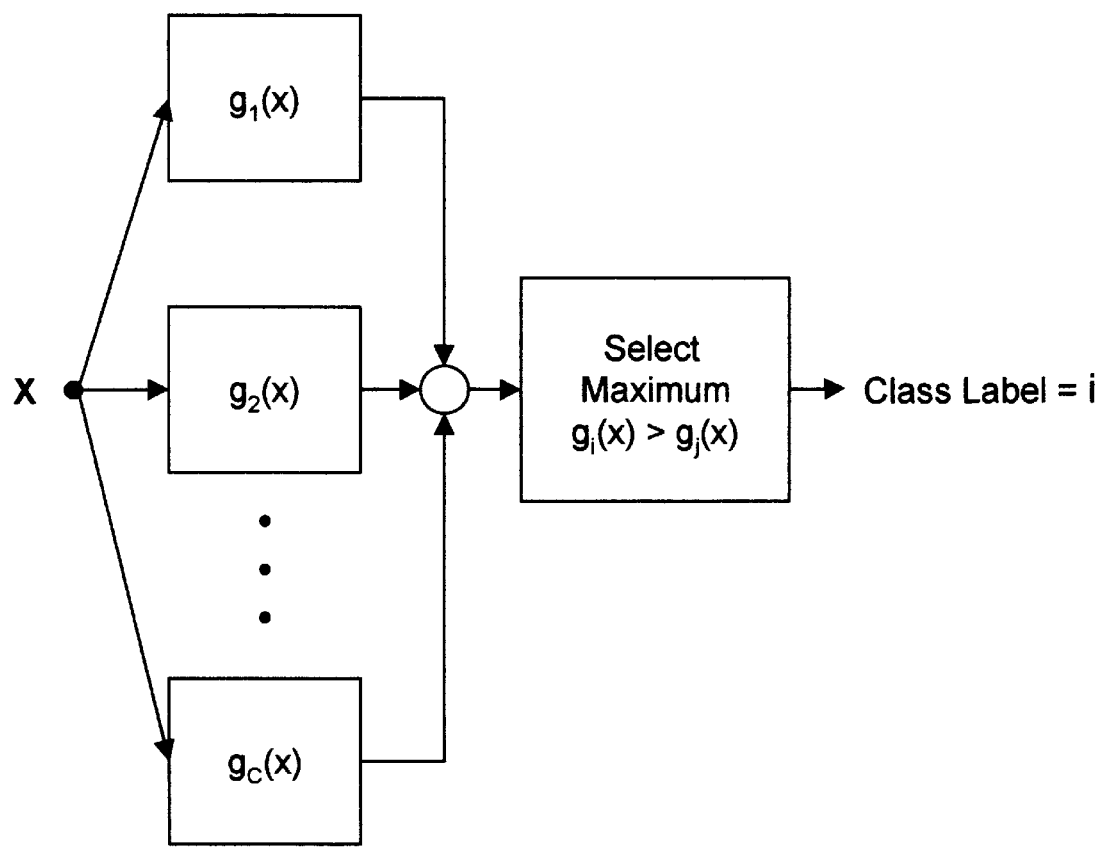
FIG. 22 is a flow diagram illustrating a classifier having one discriminant function per class.

Referring to FIG. 22, there may be seen therein a classifier having a feature vector x applied to a set of discriminant functions g(x). The classifier shown in FIG. 22 is designed with one discriminant function per class. A discriminant function computes a single value as a function of an input feature vector. Discriminant functions may be learned from training data and implemented in a variety of functional forms. The output of a discriminant function is referred to as a test statistic. Classification is selecting a class according to the discriminant function with the greatest output value. The test statistic is compared to a threshold value. For values of the test statistic above the threshold, the region or detection associated with the feature vector is retained and displayed as potentially suspicious. When the test statistic is below the threshold, the region is not displayed.

Many methods are available for designing discriminant functions. One approach considered for this invention is a class of artificial neural networks. Artificial neural networks require training, whereby the discriminant function is formed with the assistance of labeled training data.

In a preferred embodiment, the classification process is implemented by means of a multi-layer perceptron (MLP) neural network (NN). Of course, other classifier means could be used such as, for example, a statistical quadratric classifier. Only potential clustered microcalcifications classified as suspicious are retained for eventual designation for a radiologist. Alternatively, it may be desirable to iteratively loop between MLP NN analysis of the individual microcalcification detections and the microcalcification clusters.

Figure 23:
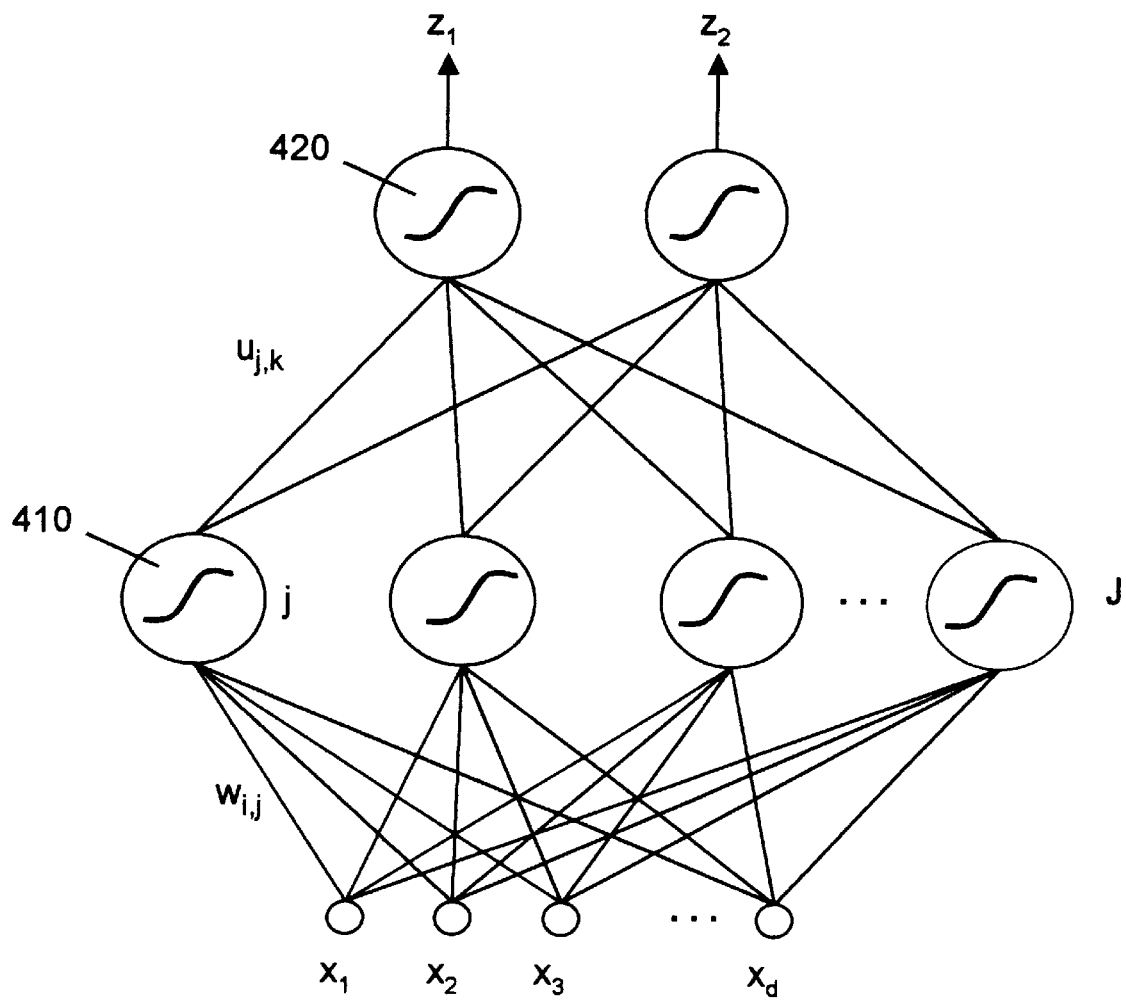
FIG. 23 is a schematic diagram illustrating a multi-layer perceptron neural network for a two-class classifier.

Referring to FIG. 23, a schematic diagram of an MLP NN may be seen therein. The MLP NN includes a first layer of J hidden layer nodes or perceptrons 410, and one output node or perceptron 420 for each class. The preferred embodiment of the invention uses two output nodes, one each for the class of suspicious detections and the class of non-suspicious detections. Of course, more or fewer classes could be used for classifying clusters of microcalcifications. Each computed feature $x_i$ is first multiplied by a weight $w_{ij}$, where i is an index representing the $i^{th}$ feature vector element, and j is an index representing the $j^{th}$ first layer node. The output $y_j$ of each first layer perceptron 410 is a nonlinear function of the weighted inputs and is given by:

$$y_j = f\left(\sum_{i=1}^{d} (w_{i,j} \times x_i)\right) \quad (8)$$

where d represents the total number of features $x_i$ and f(.) is typically a saturating nonlinearity. In this embodiment, f(.)=tanh(.). The first layer or hidden layer node outputs $y_j$ are then multiplied by a second layer of weights $u_{j,k}$ and applied to the output layer nodes 420. The output of an output layer node 420 is a nonlinear function of the weighted inputs and is given by:

$$z_k(y) = f\left(\sum_{j=1}^{J} (u_{j,k} \times y_j)\right) \quad (9)$$

where k is an index representing the $k^{th}$ output node.

The hyperbolic tangent function is used in a preferred embodiment of the system because it allows the MLP NN to be trained relatively faster as compared to other functions. However, functions other than the hyperbolic tangent may be used to provide the outputs from the perceptrons. For example, linear functions may be used, as well as smoothly varying nonlinear functions, such as the sigmoid function.

The weight values are obtained by training the network. Training consists of repeatedly presenting feature vectors of known class membership as inputs to the network. Weight values are adjusted with a back propagation algorithm to reduce the mean squared error between actual and desired network outputs. Desired outputs of $z_1$ and $z_2$ for a suspicious input are +1 and −1, respectively. Desired outputs of $z_1$ and $z_2$ for non-suspicious inputs are −1 and +1, respectively. Other error metrics and output values may also be used.

In this embodiment of the system, the MLP NN is implemented by means of software running on a general-purpose computer. Alternatively, the MLP NN could also be implemented in a hardware configuration by means readily apparent to those with ordinary skill in the art.

After training, each detected clustered microcalcification is classified as either suspicious or not suspicious by means forming the difference $z_1-z_2$, then comparing the difference to a threshold, θ. For values of $z_1-z_2$ greater than or equal to the threshold θ, i.e., $z_1-z_2 \geq \theta$, the classifier returns a value of +1 for suspicious clustered microcalcifications, and for values of $z_1-z_2<\theta$, the classifier returns a value of −1 for non-suspicious clustered microcalcifications.

In order to arrive at optimum values for the respective weights, and the number of first layer nodes, the MLP NN was trained with a training set of feature vectors derived from a database of 978 mammogram images.

To develop and test the CAD system of the invention, truth data was first generated. Truth data provides a categorization of the tissue in the digital images as a function of position. Truth data was generated by certified radiologists marking truth boxes over image regions associated with cancer. In addition to the mammogram images, the radiologists also had access to patient histories and pathology reports.

The radiologists identified 57 regions of interest, containing biopsy-confirmed cancers associated with clustered microcalcifications, by means of truth boxes. All 978 images were then processed by the microcalcification detector of the invention to produce a plurality of feature vectors, a subset of which were associated with the 57 truth boxes. Half of the subset feature vectors were randomly chosen, along with about three times as many feature vectors not associated with clustered microcalcifications, to comprise the training set of feature vectors. The MLP NN, having a predetermined number of hidden nodes, was then trained using the training set. The remaining feature vectors were used as a test database to evaluate the performance of the MLP NN after training. Training of the MLP NN was carried out by means of the Levenberg-Marquardt back propagation algorithm.

Alternatively, the MLP NN can be trained with other learning algorithms and may have nonlinearities other than the hyperbolic tangent in either or both layers. In an alternative embodiment with sigmoidal output nodes, the Bayes optimal solution of the problem of classifying clustered microcalcification detections as either suspicious or non-suspicious may be obtained.

Figure 24:
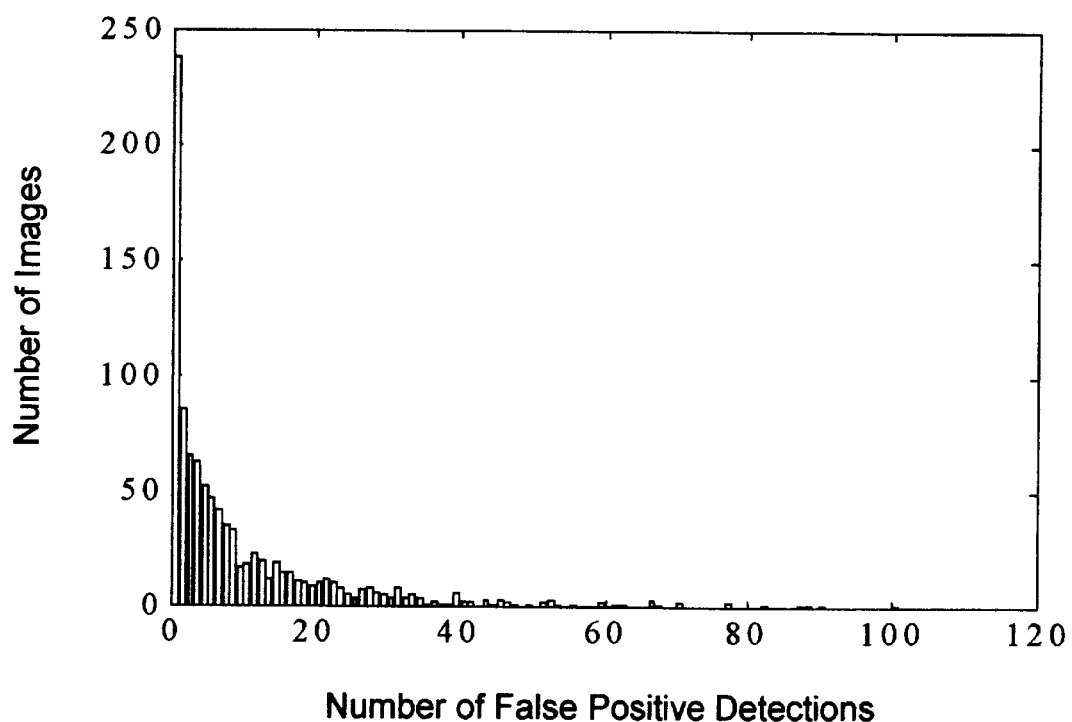
FIG. 24 is a histogram of testing results after detection and classification.

In one run of the preferred embodiment during testing, before application of the MLP NN classifier to eliminate false-positive clustered microcalcifications, the detection procedure found about 93% of the true-positive clustered microcalcifications in both the training and test databases while indicating about 10 false-positive clustered microcalcifications per image. It was found that after an MLP NN classifier having 25 first layer nodes was used with the respective optimum weights found during training, 93% of the true-positive detections were retained while 57% of the false-positive detections were successfully removed. Referring to FIG. 24, there may be seen a histogram of the results of testing on the testing database after classification by the MLP NN. Of course, the MLP NN of the invention may be operated with more or fewer first layer nodes as desired.

DISPLAYING DETECTIONS

After the locations of clustered microcalcifications have been determined, they are indicated on the original digitized mammogram image, or a copy of the original image, by drawing rectangular boxes around microcalcifications. Other means for indicating the locations of microcalcifications may be used, such as, for example, placing arrows in the image pointing at detections or drawing ellipses around the detections.

The locations of clustered microcalcifications are passed to the display detections procedure as a list of row and column coordinates of the upper left and lower right pixels bounding each of the clusters. The minimum row and column coordinates and maximum row and column coordinates are computed for each cluster. Bounding boxes defined by the minimum and maximum row and column coordinates are added to the original digitized image, by means well known in the art. The resulting image is then stored as a computer-readable file, displayed on a monitor, or printed as a hard-copy image, as desired.

In one embodiment of the system, the resulting image is saved to a hard disk on a general-purpose computer having dual Pentium II® processors and running a Windows NT® operating system. The resulting image may be viewed on a VGA or SVGA monitor, such as a ViewSonic PT813® monitor, or printed as a hard-copy gray-scale image using a laser printer, such as a Lexmark Optra S1625®. Of course, other hardware elements may be used by those with ordinary skill in the art.

OPTIMIZING THE PARAMETERS

Figure 25:
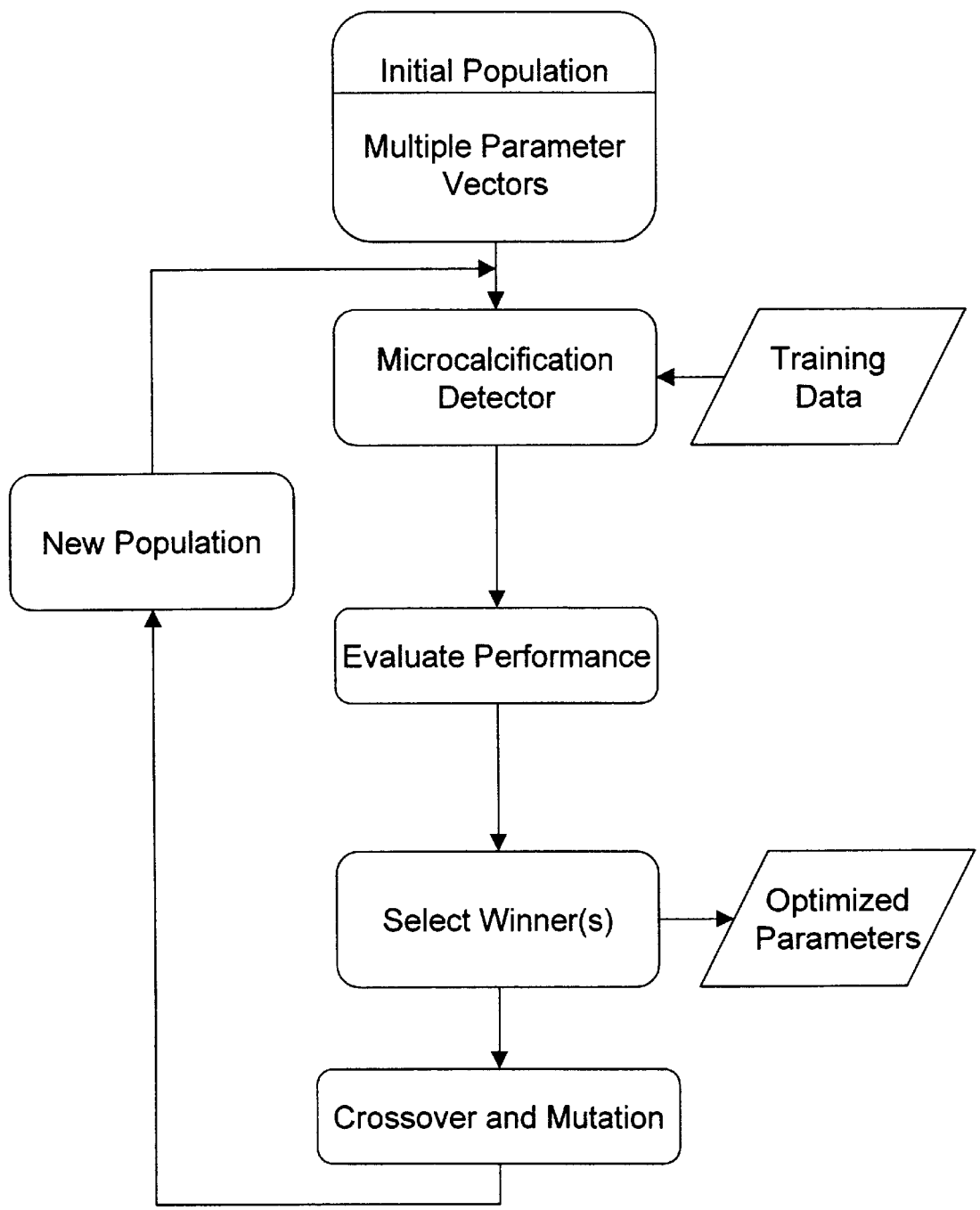
FIG. 25 is a flow diagram illustrating the parameter optimization method of the invention.

Genetic algorithms (GAs) have been successfully applied to many diverse and difficult optimization problems. A preferred embodiment of this invention uses an implementation of a GA developed by Houck, et al. ("A Genetic Algorithm for Function Optimization," Tech. Rep., NCSU-IE TR 95-09, 1995), the entire disclosure of which is incorporated by reference herein, to find promising parameter settings. The parameter optimization process of the invention is shown in FIG. 25. This is a novel application of optimization techniques as compared to current computer-aided diagnosis systems that require hand tuning by experiment.

GAs search the solution space to maximize a fitness (objective) function by use of simulated evolutionary operators such as mutation and sexual recombination. In this embodiment, the fitness function to be maximized reflects the goals of maximizing the number of true-positive detections while minimizing the number of false-positive detections. GA use requires determination of several issues: objective function design, parameter set representation, population initialization, choice of selection function, choice of genetic operators (reproduction mechanisms) for simulated evolution, and identification of termination criteria.

The design of the objective function is a key factor in the performance of any optimization algorithm. The function optimization problem for detecting clustered microcalcifications may be described as follows: given some finite domain, D, a particular set of cluster detection parameters, $x=\{t, f, k_{lo}, k_{hi}, N, \mu Cs_{min}, d_{nn}\}$ where $x \in D$, and an objective function $f_{obj}: D \to \Re$, where $\Re$ denotes the set of real numbers, find the x in D that maximizes or minimizes $f_{obj}$. When sloping local thresholding is used in the cluster detector, the parameters N, A, B, and C are optimized. Radiologic imaging systems may be optimized to maximize the TP rate subject to the constraint of minimizing the FP rate. This objective may be recast into the functional form shown in the following equation:

$$f_{obj}(x) = \begin{cases} -FP(x), & TP(x) \geq TP_{min} \\ FP_{penalty}, & \text{otherwise} \end{cases} \quad (10)$$

where maximization is the goal. For a particular set of cluster detection parameters, if the minimum acceptable TP rate, $TP_{min}$, is exceeded, the objective function returns the negative of the FP rate. Otherwise, if the TP rate falls below $TP_{min}$, the objective function returns a constant value, $FP_{penalty}=-10$. Other objective functions may also be used.

Since a real-valued GA is an order of magnitude more efficient in CPU time than the binary GA, and provides higher precision with more consistent results across replications, this embodiment of the invention uses a floating-point representation of the GA.

This embodiment also seeds the initial population with some members known beforehand to be in an interesting part of the search space so as to iteratively improve existing solutions. Also, the number of members is limited to twenty so as to reduce the computational cost of evaluating objective functions.

In one embodiment of the invention, normalized geometric ranking is used, as discussed in greater detail in Houck, et al., supra, for the probabilistic selection process used to identify candidates for reproduction. Ranking is less prone to premature convergence caused by individuals that are far above average. The basic idea of ranking is to select solutions for the mating pool based on the relative fitness between solutions. This embodiment also uses the default genetic operation schemes of arithmetic crossover and non-uniform mutation included in Houck, et al.'s GA.

This embodiment continues to search for solutions until the objective function converges. Alternatively, the search could be terminated after a predetermined number of generations. Although termination due to loss of population diversity and/or lack of improvement is efficient when crossover is the primary source of variation in a population, homogeneous populations can be succeeded with better (higher) fitness when using mutation. Crossover refers to generating new members of a population by combining elements from several of the most fit members. This corresponds to keeping solutions in the best part of the search space. Mutation refers to randomly altering elements from the most fit members. This allows the algorithm to exit an area of the search space that may be just a local maximum. Since restarting populations that may have converged proves useful, several iterations of the GA are run until a consistent lack of increase in average fitness is recognized.

Once potentially optimum solutions are found by using the GA, the most fit GA solution may be further optimized by local searches. An alternative embodiment of the invention uses the simplex method to further refine the optimized GA solution.

The autocropping system may also benefit from optimization of its parameters including contrast value, number of erodes, and number of dilates. The method for optimizing the autocropper includes the steps of generating breast masks by hand for some training data, selecting an initial population, and producing breast masks for training data. The method further includes the steps of measuring the percent of overlap of the hand-generated and automatically-generated masks as well as the fraction of autocropped breast tissue outside the hand-generated masks. The method further comprises selecting winning members, generating new members, and iterating in a like manner as described above until a predetermined objective function converges.

Figure 26:
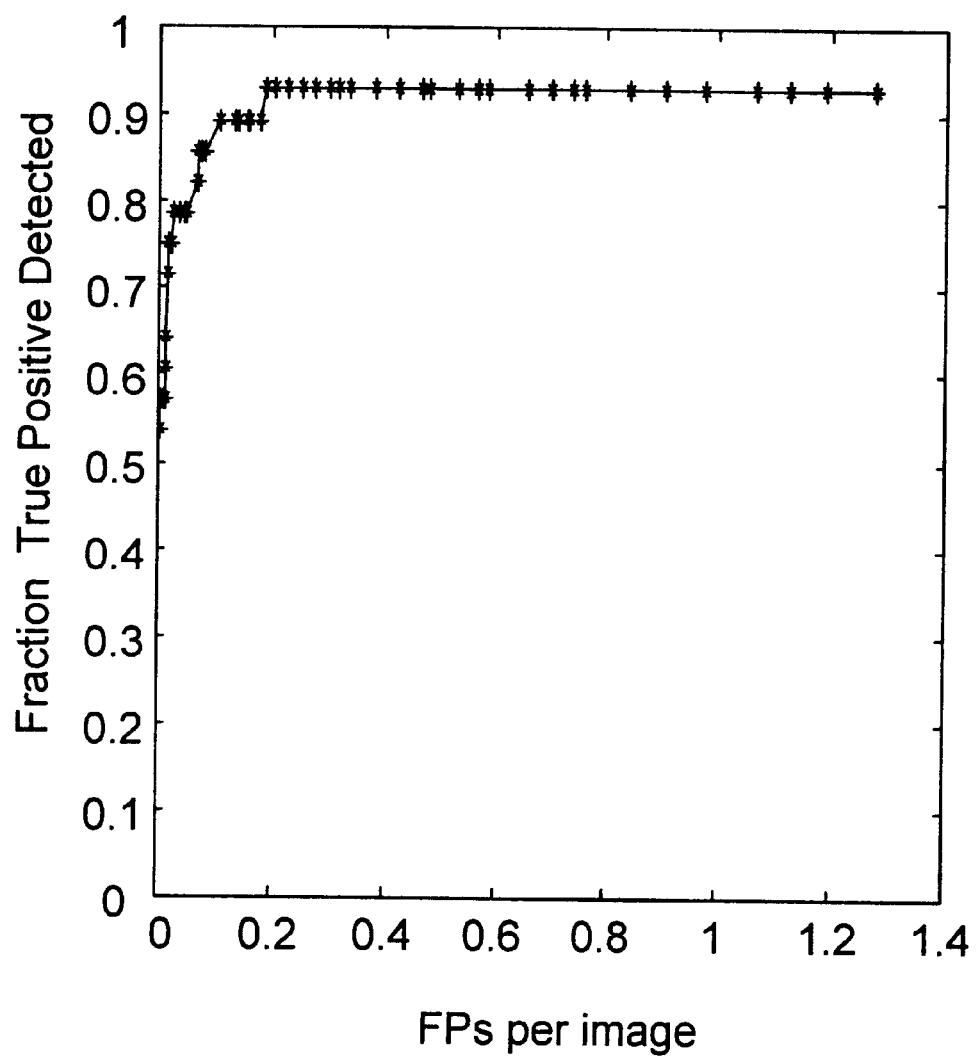
FIG. 26 is a plot of a free response receiver operating characteristic curve of the invention before classifying detections.
Figure 27:
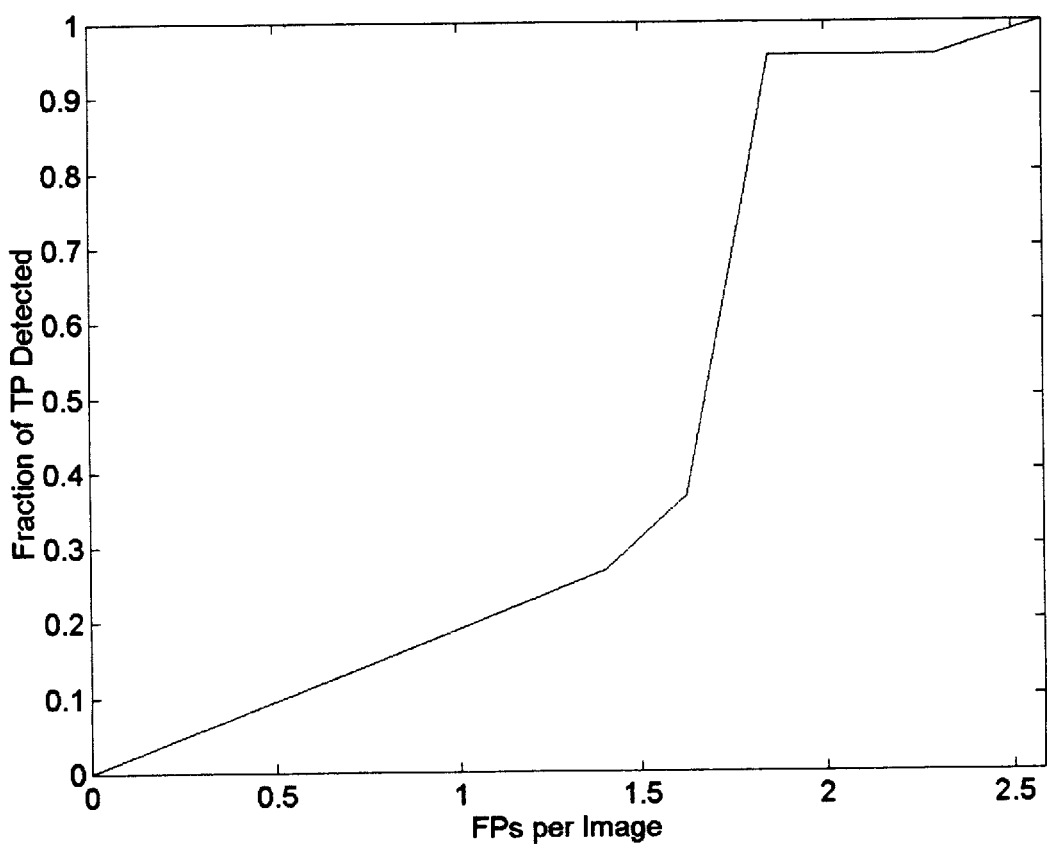
FIG. 27 is a plot of a free response receiver operating characteristic curve of the invention after classifying detections.

In FIGS. 26 and 27, there may be seen therein free response receiver operating characteristic curves for the system of the invention for the outputs of the optimized microcalcification detector and the classifier, respectively. FIG. 26 represents the performance of the optimized detector before classifying detections, while FIG. 27 represents the performance of the system after classifying detections.

Although the GA has been described above in connection with the parameter optimization portion of the preferred embodiment, other optimization techniques are suitable such as, for example, response surface methodology. Of course, processing systems other than those described herein may be optimized by the methods disclosed herein, including the GA.

INCORPORATING CAD SYSTEM OUTPUTS FOR OPTIMAL SENSITIVITY

Performance metrics for detection of suspicious regions associated with cancer are often reported in terms of sensitivity and specificity. Sensitivity measures how well a system finds suspicious regions and is defined as the percentage of suspicious regions detected from the total number of suspicious regions in the cases reviewed. Sensitivity is defined as:

$$\text{Sensitivity} = \frac{TP}{TP+FN} \quad (11)$$

where TP is the number of regions reported as suspicious by a CAD system that are associated with cancers, and FN is the number of regions that are known to be cancerous that are not reported as suspicious. Specificity measures how well the system reports normal regions as normal. Specificity is defined as:

$$\text{Specificity} = \frac{TN}{FP + TN} \quad (12)$$

where TN represents regions correctly identified as not suspicious and FP represents regions reported as suspicious that are not cancerous.

Current CAD systems increase specificity by reducing FP. However, FP and TP are coupled quantities. That is, a reduction of FP leads to a reduction of TP. This implies that some of the suspicious regions that could have been detected are missed when the objective is to maintain high specificity.

Figure 28:
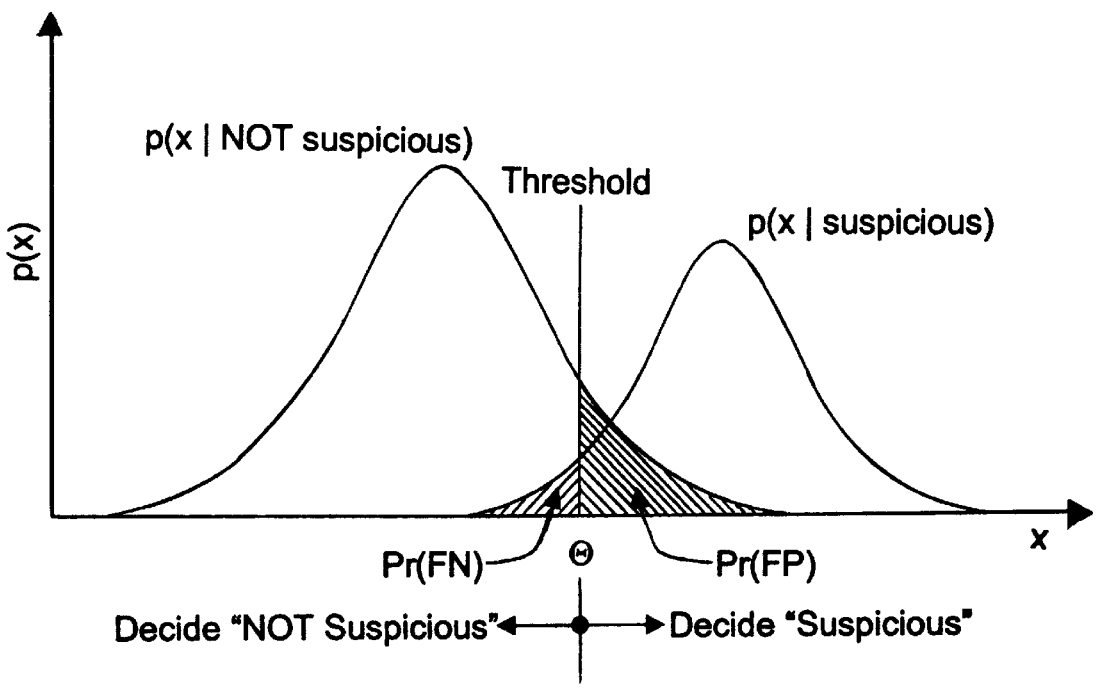
FIG. 28 is a plot of probability density functions showing the relationship between the probabilities of false negative and false positive detections.
Figure 29:
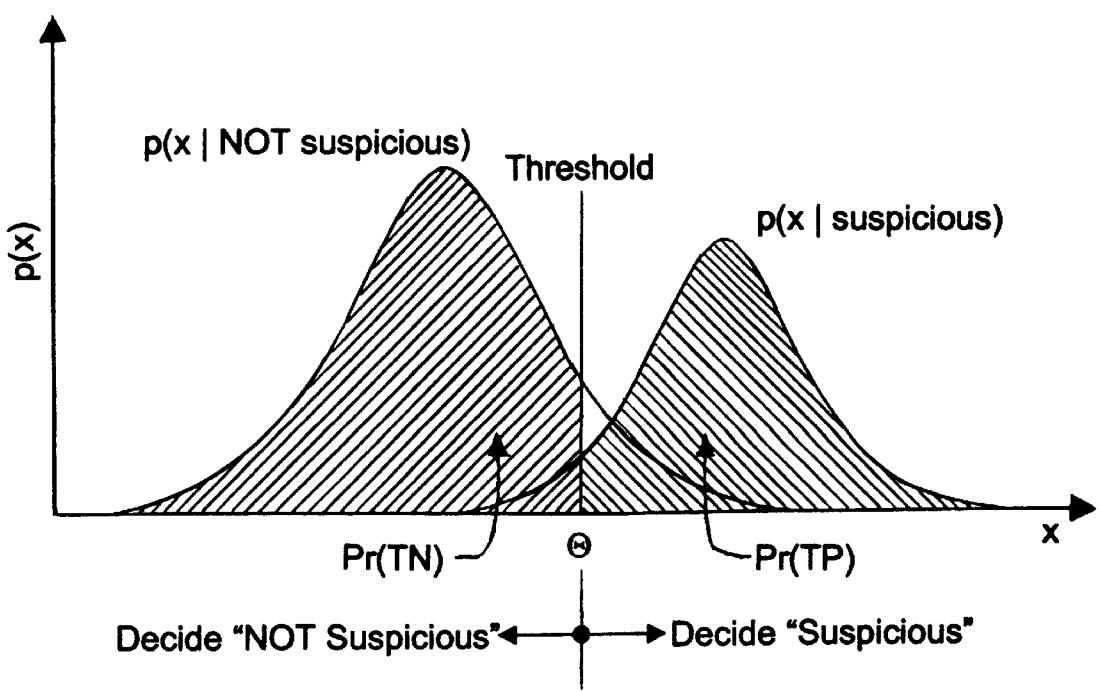
FIG. 29 is a plot of probability density functions showing the relationship between the probabilities of true negative and true positive detections.

FIGS. 28 and 29 illustrate relationships between the quantities TP, FP, TN, and FN. A measurement from a screening mammography image is represented by test statistic, x. The probability density function of x is represented by p(x) and the decision threshold is represented by θ. If x is greater than θ, a suspicious region is reported. Areas under the probability density functions represent probabilities of events. From FIG. 28 observe that increasing the threshold reduces the probability of FP decisions. However, observe from FIG. 29 that increasing the threshold simultaneously reduces the probability of TP decisions.

Another metric that exists for CAD systems is positive predictive value (PPV), which is defined as the probability that cancer actually exists when a region of interest is labeled as suspicious. PPV can be calculated from the following equation:

$$PPV = \frac{TP}{TP + FP} \quad (13)$$

Note that increasing TP or reducing FP increases PPV.

Figure 30:
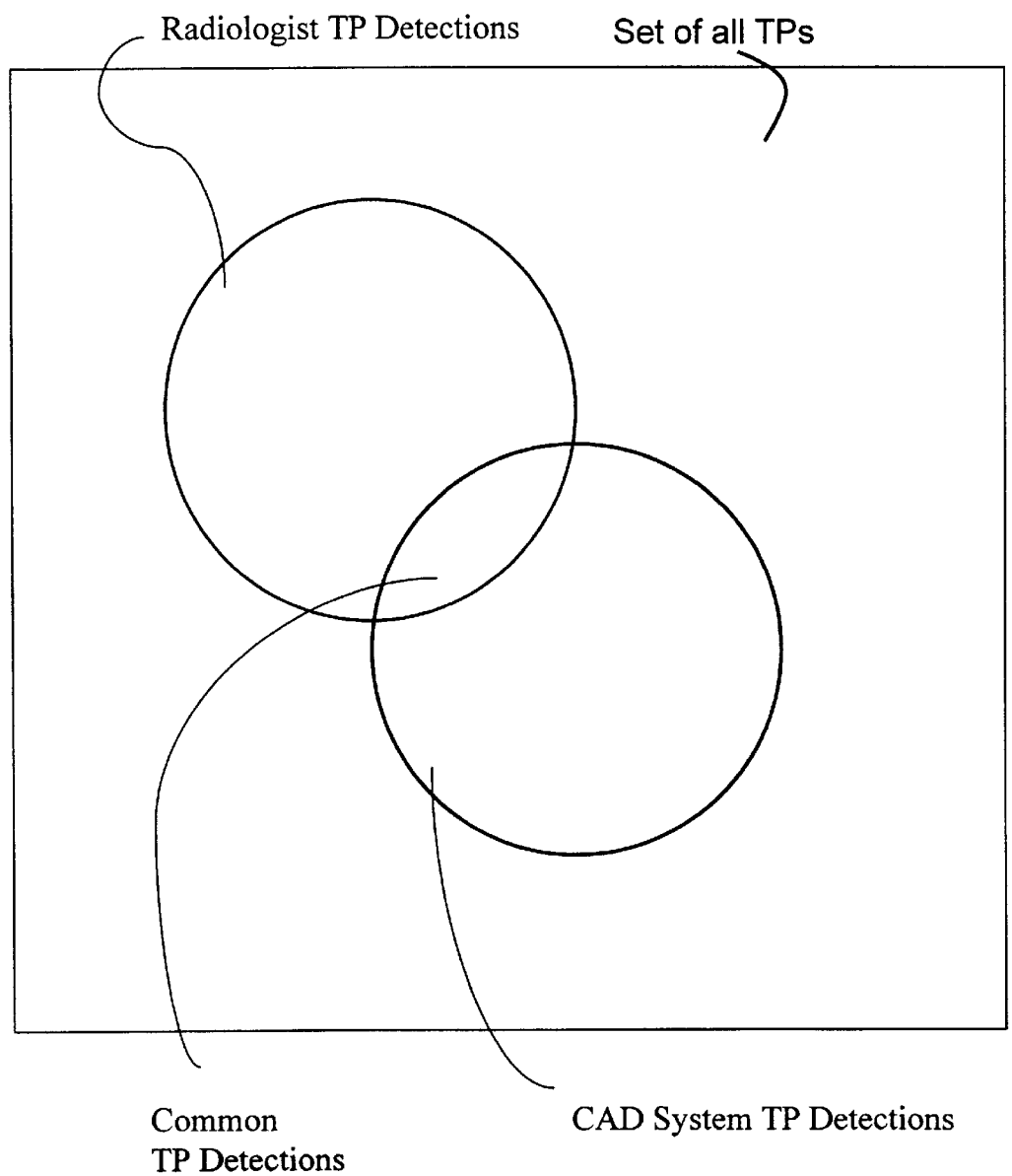
FIG. 30 is a Venn diagram showing the relationship between radiologist and CAD system detections.

Radiologists and computers find different suspicious regions. FIG. 30 is a Venn diagram depicting a possible distribution of suspicious regions for man and machine detections. Some suspicious regions are found solely by a human interpreter or radiologist, some solely by a CAD system, some are found by both, and some are not found by either.

Figure 31:
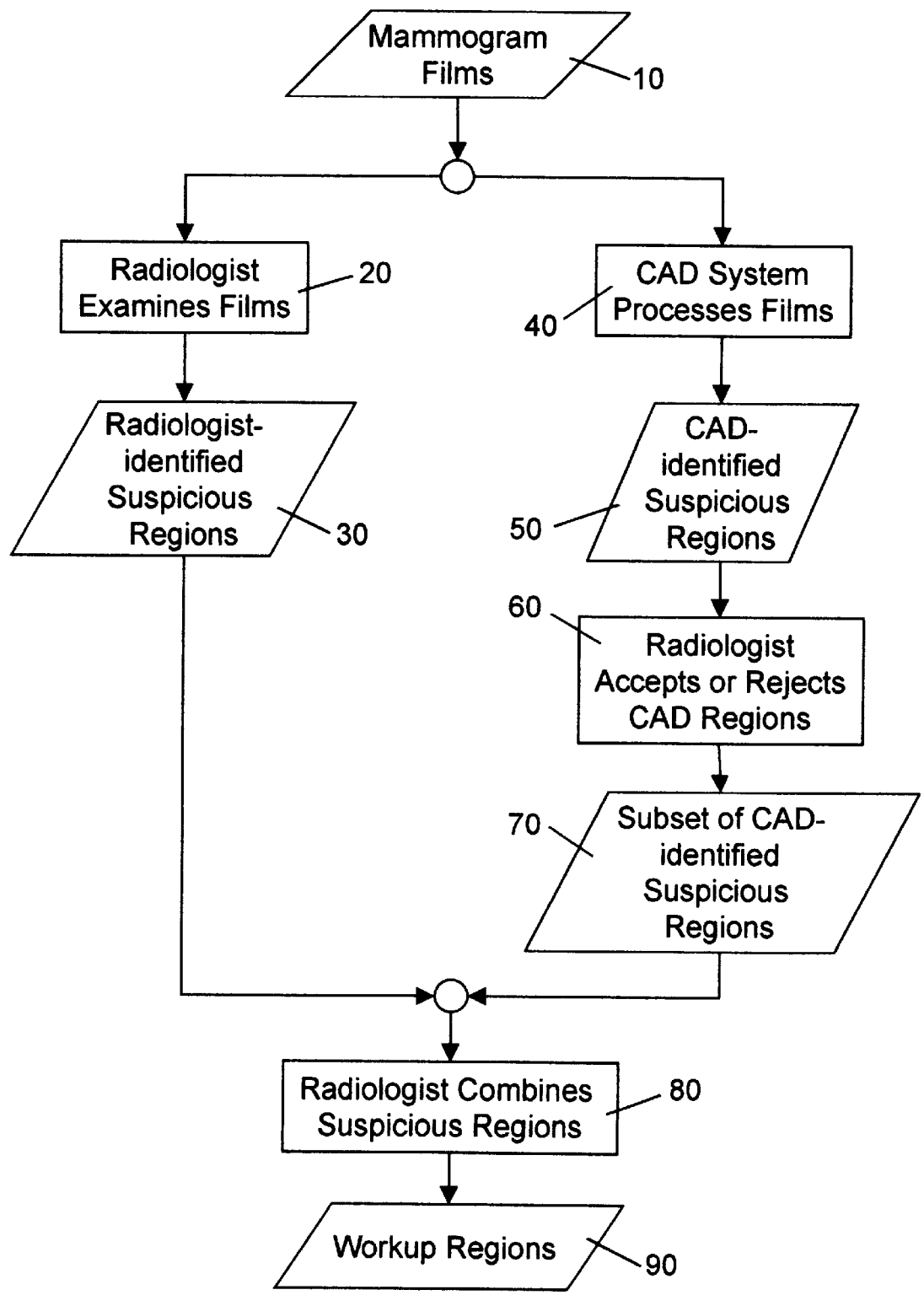
FIG. 31 is a flow diagram illustrating a method for incorporating computer-aided diagnosis detections with those of a human interpreter for optimal sensitivity.

Referring to FIG. 31, there may be seen a preferred method for incorporating the outputs of a CAD system, and more particularly for the CAD system of the invention, with the observations of a human interpreter of a screening mammography image 10 for optimal sensitivity, wherein a radiologist examines the screening mammography image 10 in a step 20 and reports a set of suspicious regions 30 designated as S1. The CAD system then operates on the image 10 in a step 40 and reports a set of suspicious regions 50 designated as S2. The radiologist then examines set S2 and accepts or rejects members of set S2 as suspicious in a step 60, thereby forming a third set of suspicious regions 70 denoted as S3, which is a subset of S2. The radiologist then creates in a step 80 a set of workup regions 90 denoted as S4 which is the union of sets S1 and S3. The workup regions 90 are then recommended for further examination such as taking additional mammograms with greater resolution, examining the areas of the breast tissue corresponding to the workup regions by means of ultrasound, or performing biopsies of the breast tissue.

While the invention has been described in connection with detecting clustered microcalcifications in mammograms, it should be understood that the methods and systems described herein may also be applicable to other medical images such as chest x-rays.

While the methods herein described constitute preferred embodiments of this invention, it is to be understood that the invention is not limited to these precise methods, and that changes may be made in these methods without departing from the scope of the invention which is defined in the appended claims.

What is claimed is:

1. A method for incorporating the output detections of a computer-aided detection system for detecting suspicious regions in a mammogram with observed detections of a human interpreter of the same mammogram without reducing sensitivity, comprising the steps of:

obtaining said observed detections to form a first set of detections;

obtaining said output detections to form a second set of detections;

accepting some output detections in said second set to form a third set of detections;

combining said first set and said third set to form a fourth set of detections; and providing an output based on said fourth set of detections.

2. The method of claim 1 wherein said some output detections accepted from said second set are selected according to their likelihood of warranting further examination.

3. The method of claim 1 wherein said suspicious regions comprises microcalcifications.

4. The method of claim I wherein said output detections are obtained from said computer-aided detection system by a method comprising the steps of:

filtering a digital representation of said mammogram to produce a second digital representation in which the appearance of microcalcifications is enhanced;

globally thresholding said second digital representation to locate a set of globally bright pixels;

locally thresholding said second digital representation to locate a set of locally bright pixels; and generating a third digital representation of those pixels which are common to both said sets of bright pixels.

5. A method for incorporating the output detections of a computer-aided detection system for detecting suspicious regions in a mammographic image with observed detections of a human interpreter of the same mammographic image without reducing sensitivity, comprising the steps of:

combining said output detections and said observed detections by forming the union thereof to produce set of maximally sensitive detections; and providing an output indicative of said set of maximally sensitive detections.

6. The method of claim 5 wherein said suspicious regions comprise micro calcifications.

7. The method of claim 5 wherein said output comprises a visual representation of said mammogram with indicia appearing therein indicating the locations of suspicious regions therein.

* * * * *